United States Patent
De Sausmarez Lintell et al.

(10) Patent No.: US 9,333,302 B2
(45) Date of Patent: May 10, 2016

(54) DRUG DELIVERY DEVICE HAVING A COLLAR AND A LINKAGE COMPONENT

(75) Inventors: Daniel Thomas De Sausmarez Lintell, Warwickshire (GB); Garen Kouyoumjian, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 295 days.

(21) Appl. No.: 13/885,828

(22) PCT Filed: Nov. 28, 2011

(86) PCT No.: PCT/EP2011/071143
§ 371 (c)(1),
(2), (4) Date: May 16, 2013

(87) PCT Pub. No.: WO2012/072565
PCT Pub. Date: Jun. 7, 2012

(65) Prior Publication Data
US 2013/0245566 A1    Sep. 19, 2013

(30) Foreign Application Priority Data
Nov. 29, 2010   (EP) ..................................... 10192846

(51) Int. Cl.
*A61M 5/315* (2006.01)
*A61M 5/19* (2006.01)
(Continued)

(52) U.S. Cl.
CPC ............. *A61M 5/31548* (2013.01); *A61M 5/19* (2013.01); *A61M 5/20* (2013.01); *A61M 5/3156* (2013.01);
(Continued)

(58) Field of Classification Search
CPC ..... A61M 5/19; A61M 5/20; A61M 5/31596; A61M 5/31575; A61M 5/31583; A61M 5/31585
See application file for complete search history.

(56) References Cited

U.S. PATENT DOCUMENTS

| 5,253,785 A | 10/1993 | Haber et al. |
| 5,505,704 A | 4/1996 | Pawelka et al. |

(Continued)

FOREIGN PATENT DOCUMENTS

| DE | 19930631 | 1/2001 |
| GB | 852572 | 10/1960 |

(Continued)

OTHER PUBLICATIONS

International Preliminary Report on Patentability for Int. App. No. PCT/EP2011/071143, mailed Jun. 13, 2013.

(Continued)

*Primary Examiner* — Nathan R Price
*Assistant Examiner* — Melissa A Snyder
(74) *Attorney, Agent, or Firm* — McDonnell Boehnen Hulbert & Berghoff LLP

(57) ABSTRACT

A drug delivery device having a collar and a linkage component. The drug delivery device includes a variable dose setting mechanism, a fixed dose setting mechanism, a single dose setter, a collar, and a linkage component. The variable dose setting mechanism is operably coupled to a primary reservoir holding a first medicament and/or fluid. The fixed dose setting mechanism comprises a fixed dose piston rod that is operably coupled to a secondary reservoir holding a second medicament and/or fluid. Further, the single dose setter is operably coupled to the variable dose setting mechanism, and the collar is disposed on the variable dose setting mechanism. Still further, the linkage component may be disposed on the fixed dose setting mechanism, wherein the linkage component is capable of engagement with the collar. The delivery device is capable of delivering the second medicament and/or fluid by way of at least one discrete pulse of the second medicament and/or fluid.

14 Claims, 16 Drawing Sheets

(51) Int. Cl.
*A61M 5/20* (2006.01)
*A61M 5/34* (2006.01)
*A61M 5/178* (2006.01)
*A61M 5/24* (2006.01)

(52) U.S. Cl.
CPC ......... *A61M 5/3158* (2013.01); *A61M 5/31551* (2013.01); *A61M 5/31561* (2013.01); *A61M 5/31563* (2013.01); *A61M 5/31585* (2013.01); *A61M 5/2053* (2013.01); *A61M 5/31575* (2013.01); *A61M 5/34* (2013.01); *A61M 2005/1787* (2013.01); *A61M 2005/208* (2013.01); *A61M 2005/2013* (2013.01); *A61M 2005/2474* (2013.01)

(56) References Cited

U.S. PATENT DOCUMENTS

| | | | |
|---|---|---|---|
| 5,582,598 A | | 12/1996 | Chanoch |
| 5,584,815 A | * | 12/1996 | Pawelka et al. ............... 604/191 |
| 2004/0011816 A1 | | 1/2004 | Muhlgauer et al. |
| 2010/0094205 A1 | | 4/2010 | Boyd et al. |

FOREIGN PATENT DOCUMENTS

| | | |
|---|---|---|
| JP | H08-103495 | 4/1996 |
| JP | H08-503385 | 4/1996 |
| JP | H08-503874 | 4/1996 |
| JP | 2826196 | 11/1998 |
| JP | 2000-262525 | 9/2000 |
| WO | 94/03392 | 2/1994 |
| WO | 94/22507 | 10/1994 |
| WO | 2010/053569 | 5/2010 |

OTHER PUBLICATIONS

International Search Report and Written Opinion for Int. App. No. PCT/EP2011/071143, completed Jan. 5, 2012.

Japanese Office Action for JP App. No. 2013-540406 dated Oct. 6, 2015.

* cited by examiner

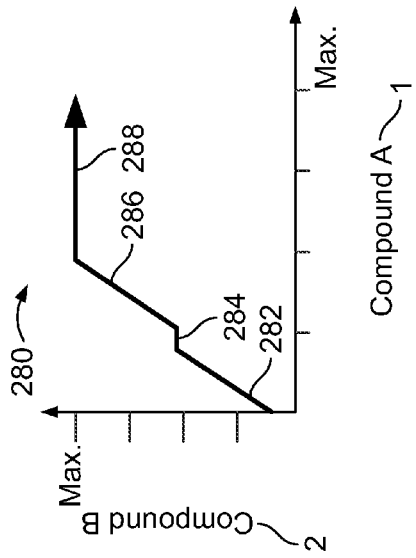
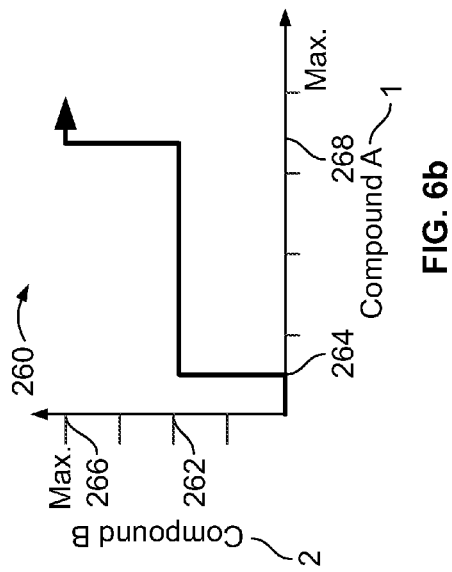
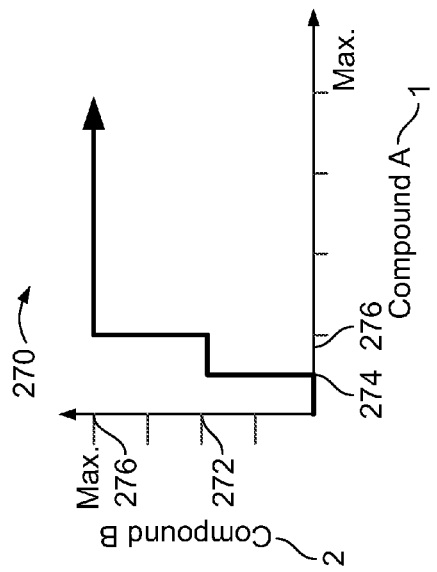

DRUG DELIVERY DEVICE HAVING A COLLAR AND A LINKAGE COMPONENT

CROSS REFERENCE TO RELATED APPLICATIONS

The present application is a U.S. National Phase Application pursuant to 35 U.S.C. §371 of International Application No. PCT/EP2011/071143 filed Nov. 28, 2011, which claims priority to European Patent Application No. 10192846.3 filed Nov. 29, 2010. The entire disclosure contents of these applications are herewith incorporated by reference into the present application.

FIELD OF THE DISCLOSURE

This present patent application relates to drug delivery devices and methods of delivering at least two drug agents from separate reservoirs using devices having only a single dispense interface. The drug agents are contained in two or more multiple dose reservoirs, containers or packages, each containing independent (single drug compound) or premixed (co-formulated multiple drug compounds) drug agents. The disclosed method and system is of particular benefit where the therapeutic response can be optimized for a specific target patient group, through control and definition of the therapeutic profile. More particularly, the disclosed method and system is of particular benefit where one of the two drug agents is administered by way of at least one discrete pulse of medicament.

BACKGROUND

Certain disease states require treatment using one or more different medicaments. Some drug compounds need to be delivered in a specific relationship with each other in order to deliver the optimum therapeutic dose. The disclosed method and system is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example, one or more actives may require a titration period to gradually introduce a patient to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems may arise where a multi-drug compound therapy is required, because certain users cannot cope with having to use more than one drug delivery system or make the necessary accurate calculation of the required dose combination. This is especially true for users with dexterity or computational difficulties.

Accordingly, there exists a strong need to provide devices and methods for the delivery of two or more medicaments in a single injection or delivery step that is simple for the user to perform. The disclosed method and system overcomes the above-mentioned problems by providing separate storage containers for two or more active drug agents that are then only combined and/or delivered to the patient during a single delivery procedure. Setting a dose of one medicament automatically fixes or determines the dose of the second medicament (i.e. non-user settable).

The disclosed method and system also gives the opportunity for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime. Alternatively, the second fluid quantity can be changed by varying the properties of the fixed dose mechanism, such as a linkage component dispose on a fixed dose setting mechanism. The disclosed system and method may achieve a wide variety of target therapeutic profiles. For example, the disclosed system and method may achieve a therapeutic dose profile that delivers a fixed dose of a secondary medicament once a minimum setting threshold dose of a primary medicament has been set. As another example, the disclosed system and method may achieve a stepped fixed dose profile. As another example, the disclosed system and method may provide for the continuous administration of a variable dose of a first or primary medicament in combination with a pulsed or incremental administration of a fixed dose. Specifically, the disclosed system and method, in one arrangement, provides a means of selecting and delivering a combination dose of a user selectable dose of a first medicament with a non-user settable dose of a second medicament, wherein the delivery of the second medicament is 'pulsed' during delivery (e.g., sequential delivery) of the first medicament.

These and other advantages will become evident from the following more detailed description of the invention.

SUMMARY

The disclosed system and method allows complex combination of multiple drug compounds within a single device. In particular, the disclosed system and method allows the user to set and dispense a multi-drug compound device through a single dose setter and a single dispense interface. The drug delivery system includes a variable dose setting mechanism and a fixed dose setting mechanism. The system also includes a collar disposed on the variable dose setting mechanism and a linkage component disposed on the fixed dose setting mechanism, where the linkage component is capable of engagement with the collar. In an example, the single dose setter controls the dose setting mechanisms of the device such that a predefined combination of the individual drug compounds is delivered when a single minimum dose of one of the medicaments is set and dispensed through the single dispense interface.

By defining the therapeutic relationship between the individual drug compounds, Applicants' delivery device would help ensure that a patient/user receives the optimum therapeutic combination dose from a multi-drug compound device without the inherent risks associated with multiple inputs, where the user has to calculate and set the correct dose combination every time they use the device. The medicaments can be fluids, defined herein as liquids, gases or powders that are capable of flowing and that change shape at a steady rate when acted upon by a force tending to change its shape. Alternatively, one of the medicaments may be a solid that is carried, solubilized or otherwise dispensed with another fluid medicament.

This disclosed system is of particular benefit to users with dexterity or computational difficulties as the first variable input and second controlled/limited input (and the associated controlled therapeutic profile) removes the need for them to calculate their prescribed dose every time they use the device and this arrangement allows considerably easier setting and dispensing of the combined compounds.

In an embodiment of the proposed system, a master drug compound, such as insulin, is contained within a primary reservoir and a secondary medicament is contained within a secondary reservoir. Although Applicants' present patent application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with Applicants' proposed system and method.

For the purposes of Applicants' system and method the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg (B32) human insulin; Lys(B3), Glu(B29) human insulin; Lys (B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys- Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

One embodiment of Applicants' disclosure relates to a drug delivery system to deliver two or more medicaments through a single dispense interface, where the device has a housing containing a first user-operable dose setter operably connected to a primary reservoir of a first medicament containing multiple doses of at least one drug agent. The device also contains a second dose setting mechanism operably connected to a second reservoir of a second medicament containing multiple doses of at least one drug agent. A dose button is operably connected to the primary reservoir of medicament and a single dispense interface is configured for fluid communication with the primary reservoir. The secondary reservoir of a second medicament containing multiple fixed doses of at least one drug agent is configured for fluid communication to the single dispense interface.

This dose button can be any type of mechanism that triggers the delivery procedure, whether driven mechanically or through a combination of electronics and mechanics. The button can move or be a touch sensitive virtual button, for example, a touch sensitive screen. Applicants' system has a single dispense interface configured for fluid communication with the primary reservoir and with a secondary reservoir of medicament containing at least one drug agent. The drug dispense interface can be any type of outlet that allows the two or more medicaments to exit the system and be delivered to the patient. Types of interfaces include hollow needles, catheters, atomizers, pneumatic injectors, or needle-less injectors, mouthpieces, nasal-applicators and the like interfaces.

Preferably, the secondary reservoir preferably contains multiple fixed doses of medicament but alternatively could also contain a single fixed dose of medicament. As mentioned above, the system is designed such that a single activation of the dose button causes the user set dose of medicament from the primary reservoir and a non-user set dose of medicament from the second reservoir to be expelled through the single dispense interface. By user settable dose it is meant dose that the user (patient or health care provider) can physically manipulate the device to set a desired dose. Additionally, the user settable dose can be set remotely through the use of wireless communication (Bluetooth, WiFi, satellite, etc.) or the dose could be set by another integrated device, such as a blood glucose monitor after performing a therapeutic treatment algorithm. By non-user set dose it is meant that the user (or any other input) cannot independently set or select a dose of medicament from the secondary reservoir. In other words, when the user (or another input as described above) sets the dose of the primary medicament in the primary reservoir, the fixed dose of the second medicament is automatically set. However, in some examples, it may be possible for a user to adjust the device prior to setting a dose in order to alter the threshold dose where the fixed dose will be set.

In an example of Applicants' proposed system, a drug delivery device includes a variable dose setting mechanism, a fixed dose setting mechanism, a single dose setter, a collar, and a linkage component. The variable dose setting mechanism is operably coupled to a primary reservoir holding a first medicament. The fixed dose setting mechanism comprises a fixed dose piston rod that is operably coupled to a secondary reservoir holding a second medicament. Further, the single dose setter is operably coupled to the variable dose setting mechanism. Still further, the collar is disposed on the variable dose setting mechanism, and the linkage component is disposed on the fixed dose setting mechanism. The linkage component is capable of engagement with the collar.

In an example, the collar is a ring-shaped collar having a gap between a first end of the collar and the second end of the collar, wherein the collar comprises a groove, and wherein the linkage component comprises a pin that is slidably engageable with the groove. In another example, the collar comprises a groove having a plurality of sections, wherein a first section is a generally flat section and a second section is a helical section, and wherein the linkage component comprises a pin that is slidably engageable with the groove. In yet another example, the collar comprises a first section having a first groove projection and a second section having a second groove projection, wherein the linkage component is capable of engagement with the first groove projection after a first minimum dose of the first medicament is set, and wherein the linkage component is capable of engagement with the second groove projection after a second minimum dose higher than the first minimum dose is set.

Applicants' present disclosure also covers a method of dispensing a fixed dose of one medicament and a variable dose of another medicament from separate reservoirs that involves the steps of first setting a dose of a first medicament contained in a primary reservoir of a drug delivery device having a single dose setter. This setting of the first dose automatically sets the dose from a secondary reservoir (e.g., after a minimum first dose threshold is exceeded) without a separate input by the user. Next a dose button is activated that moves both the set dose of the first medicament from the primary reservoir and the automatically set non-user settable dose from the secondary reservoir through a single dispense interface. Preferably, the non-user settable dose from the secondary reservoir is administered by way of at least one discrete pulse during the administration process.

The combination of compounds as discrete units or as a mixed unit can be delivered to the body via an integral needle. This would provide a combination drug injection system that, from a user's perspective, would be achieved in a manner that very closely matches the currently available injection devices that use standard needles. One possible delivery procedure would involve the following steps:

1. Attach a single dispense interface, such as a needle hub, to the distal end of the injection device such that the proximal end of the single dispense interface is in fluidic communication with both the first medicament and second medicament.
2. Dial up (i.e., set) the injection device such that it is ready to dispense the desired dose of the first medicament. As the single dose setter sets the dose of the first medicament, a predefined non-user settable dose of the second medicament can be set at the same time if a certain predefined minimum dose of the first medicament is selected.
3. Insert or apply the distal end of the single dispense interface to the patient at or into the desired administration site. Dose the first medicament by activating a single dose button, which also causes the second medicament to automatically dispense in discrete pulses.

Delivery of the second medicament in discrete pulses has certain advantages. For example, pulsed delivery may be preferable for situations where the two compounds need to be delivered together, but where the pharmacokinetics of the therapy might be improved if the mixing of the two compounds 'in vivo' is actively promoted/assisted (i.e. having a single 'slug' or discrete pulse of the secondary medicament delivered alongside the dose of the primary medicament, either at the start or end of the delivery stroke, is less desirable than splitting the dose of the secondary medicament into a series of small parts and delivering them at spaced intervals during the dispense stroke). For example, this may be caused if the 2 compounds are generally not miscible.

A particular benefit of Applicants' proposed system and method is that the use of two multi-dose reservoirs makes it is possible to tailor dose regimes when required, especially where a titration period is necessary for a particular drug. In an example, a set of drug delivery devices may be provided that have second dose setting mechanisms and/or reservoirs that have different properties, and thus result in different fixed doses of a second medicament. The drug delivery devices could be supplied in a number of titration levels with obvious differentiation features such as, but not limited to, aesthetic design of features or graphics, numbering etc, so that a user could be instructed to use the supplied drug delivery devices in a specific order to facilitate titration. Alternatively, the prescribing physician may provide the patient with a number of "level one" titration drug delivery devices and then when these were finished, the physician could then prescribe the next level.

A further feature of an example of Applicants' proposed system and method is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant, or who have dexterity or computational difficulties. The use of one injection instead of two reduces the possibility for user errors and so may increase patient safety.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIGS. 6a-c illustrate example possible dose profiles achievable with the drug delivery device illustrated in FIG. 4;

FIGS. 7a-b illustrate example possible dose profiles achievable with another drug delivery device in accordance with an example of Applicants' disclosure;

DETAILED DESCRIPTION

The drug delivery system of the present disclosure administers a combined dose that includes a variable dose of a first medicament (primary drug compound) and a fixed dose of a second medicament (secondary drug compound). This combined dose is delivered by continuously delivering the first medicament throughout the dose administration procedure while delivery of the second medicament occurs by way of one or more discrete pulses during this same procedure. Administration takes place through a single output or drug dispense interface. Setting the dose of the primary medicament by the user can set a first fixed dose of the second medicament once a minimum or first threshold dose of the primary medicament is achieved. If the user sets a dose equal to a second threshold dose of the primary medicament (i.e., one greater than the first threshold dose), a second fixed dose of the second medicament may be achieved. In an example, the drug dispense interface is a needle cannula (hollow needle).

Figure 1:
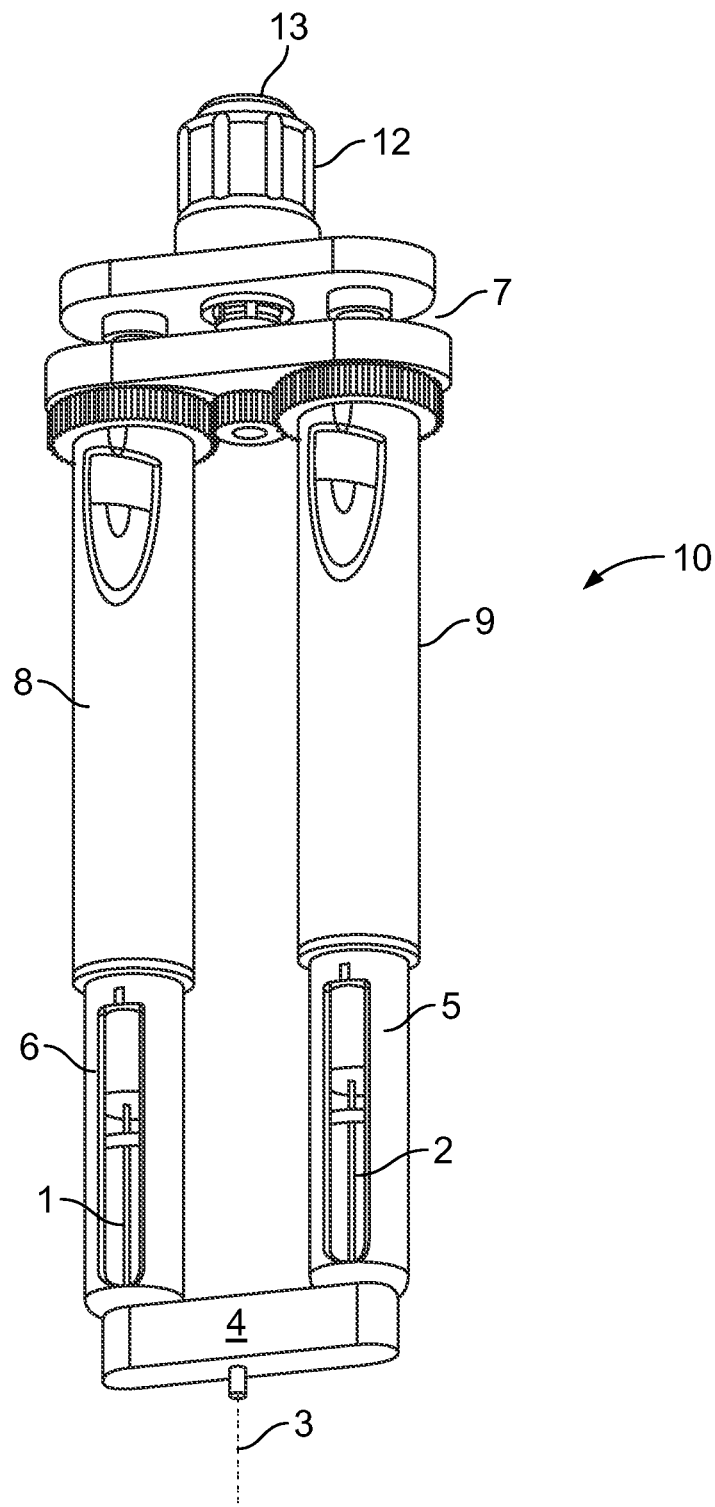
FIG. 1 illustrates an example drug delivery system, the drug delivery system having two multi-dose reservoirs positioned side-by-side containing a first medicament and a second medicament, respectively.

FIG. 1 generally illustrates a multi-dose injection device that is capable of setting and delivering both a dose of a first medicament and a second medicament via a single dose setter and a single dispense interface. The multi-dose injection device may include a mechanical link that links a variable dose setting mechanism to a fixed dose setting mechanism. According to an example of Applicants' proposed concept, the mechanical link may comprise a collar on the variable dose setting mechanism and a linkage component on the fixed dose setting mechanism. Example drug delivery devices having a collar disposed on the variable dose setting mechanism and a linkage component on the fixed dose setting mechanism are described with reference to FIGS. 2, 4, and 8. These example drug delivery devices are capable of achieving a wide variety of desired therapeutic dose profiles.

Returning to FIG. 1, FIG. 1 illustrates one possible example drug delivery system, where a multi-use injection device 10 has two reservoirs that are positioned side-by-side with one containing a first medicament 1 and the other a second medicament 2. These reservoirs may contain multiple doses of each medicament. Each reservoir may be self-contained and provided as sealed and sterile cartridges. These cartridges can be of different volumes and replaceable when empty or they can be fixed (non-removable) in the system. They can also have pierceable seals or septa to accept needle cannula.

The cartridges may be housed in cartridge holders 5 and 6 that have attachment means compatible with a removable, disposable hub or housing 4 that contains the single dispense interface. In this example the single dispense interface is shown as output needle 3. The hub can be of any design, provided that it allows for fluid communication between the primary and secondary medicaments and the single dispense interface or needle 3. An example design of hub 4 would include what is generally referred to in the art as a "2-to-1 needle" configuration. Although not shown, hub 4 could be supplied by a manufacturer contained in a protective and sterile capsule or container where the user would peel or tear open a seal or the container itself to gain access to the sterile single dispense interface. In some instances it might be desirable to provide two or more seals for each end of the hub. The seal may allow display of information required by regulatory labeling requirements. When a needle is used to deliver the medicaments it is preferred that the hub is designed to be economical and safe for allowing the user to attach a new hub for each injection. Attachment of hub 4 to the multi-use device 10 creates a fluid connection between output needle 3 and medicaments 1 and 2.

The example in FIG. 1 uses a rotational coupling 7 to mechanically link two dose delivery assemblies 8 and 9 in such a way that rotation of single dose setter 12 allows the user to select a dose of the primary medicament 1 and automatically set a fixed or predetermined non-user settable dose of secondary medicament 2. In the embodiment illustrated, the rotational coupling 7 has been embodied as a gear train in which counter-clockwise rotation of the single dose setter causes clockwise rotation of dose dial components (not shown) within the dose delivery assemblies 8 and 9. Rotational coupling 7 may be constructed such that it moves vertically at the same rate as both of the dial components. This allows it to set and dispense both drug compounds throughout the full operational range of the device.

As generally understood by those skilled in the art, it may be convenient to use lead screws or spindles to push on or drive a piston or bung contained within a cartridge of medicament. As such, spindles may be used in each dose delivery assembly. By varying the spindle pitches it is possible to vary the dose sizes (and dose ratio) in relation to each other. Specifically, this allows variation of the therapeutic profile to suit a specific therapy or patient requirements by providing devices with different dose ratios. The device shown in FIG. 1 could be operated as follows:

a. Counter-clockwise rotation of the dose setter 12 causes counter-clockwise rotation of the drive gear and clockwise rotation of both driven gears in rotational coupling 7. Clockwise rotation of both driven gears forces both dial components in dose delivery assemblies 8 and 9 to rotate in the same direction and follow a helical path out of the body of the device. This operation allows the user to set a target dose of medicament 1, but not medicament 2, which is automatically set by the dose selected for medicament 1.

b. Initiation of the dosing phase begins with the actuation of dispense or dose button 13. This causes the dial components to rotate independently of the dose setter.

c. During the dosing phase, the direction of rotation of the single dose setter as well the internal components of both device mechanisms is reversed. The rotational coupling 7 moves back towards the body of the device as both dial components wind back into the mechanisms following their respective helical paths. This reversal of rotation of both mechanisms coupled with the internal overhauling of the spindles by internal drive sleeves (not shown) causes both medicaments to be dispensed in a simultaneous fashion following the fixed ratio profile defined when the user set the target dose of medicament 1.

Varying the spindle pitches of the individual device mechanisms in relation to each other may alter the relationship of the fixed ratio of medicaments. Variation of the spindle pitch changes the advance of the spindle during dispense for a given amount of rotation during setting. Differing amounts of advance between the two mechanisms has the effect of creating different dispense ratios between the mechanisms. Variation of the spindle pitches may have the effect of extending the operational window of delivery device 10 in terms of the range of fixed ratios that can be achieved. This may also assist in keeping the spindle pitch in a range that allows resetting should the device be required to be reusable. This means that multiple pen injectors each having a different therapeutic profile can be manufactured. Specifically, this allows variation of the therapeutic profile to suit a specific titration regime and ultimately individual patient requirements.

The attachment means between hub 4 and cartridge holders 5 and 6 can be those known to those skilled in the art, including threads, snap locks, snap fits, luer locks, bayonet, snap rings, keyed slots, and combinations of such connections. The connection or attachment between the hub and the cartridge holder may also contain additional features (not shown), such as connectors, stops, splines, ribs, grooves, pips, clips and the like design features, that ensure that specific hubs are attachable only to matching drug delivery devices.

The shape of the dispense device 10, including hub 4, may be generally oval and/or cylindrical or any other geometric shape suitable for hand manipulation by a user. Additionally, hub 4 could incorporate a safety shield device that would prevent accidental needle sticks and reduce the anxiety experienced by users who suffer from needle phobia. The exact design of the safety shield is not critical to the drug delivery device, however, an example design is one that is operably connected to the first and/or second reservoirs. In such a design the activation of the safety shield could unlock the drug delivery system or instigate fluid communication between the reservoirs and in some cases cause the second medicament to be dispensed prior to activating the dose button to dispense the primary medicament from the first reservoir. Another example design would physically prevent insertion of the used drug dispense interface into the patient (e.g. a single use needle-guard type arrangement).

As mentioned an example design of Applicants' drug delivery device would include cartridges to contain the medicaments. Cartridges are typically cylindrical in shape and are usually manufactured in glass, sealed at one end with a rubber bung (piston) and at the other end by a rubber septum using a metal ferrule. The dose delivery assemblies are typically powered by a manual action of the user. However, the injection mechanism may also be powered by other means such as a spring, compressed gas or electrical energy.

Figure 2:
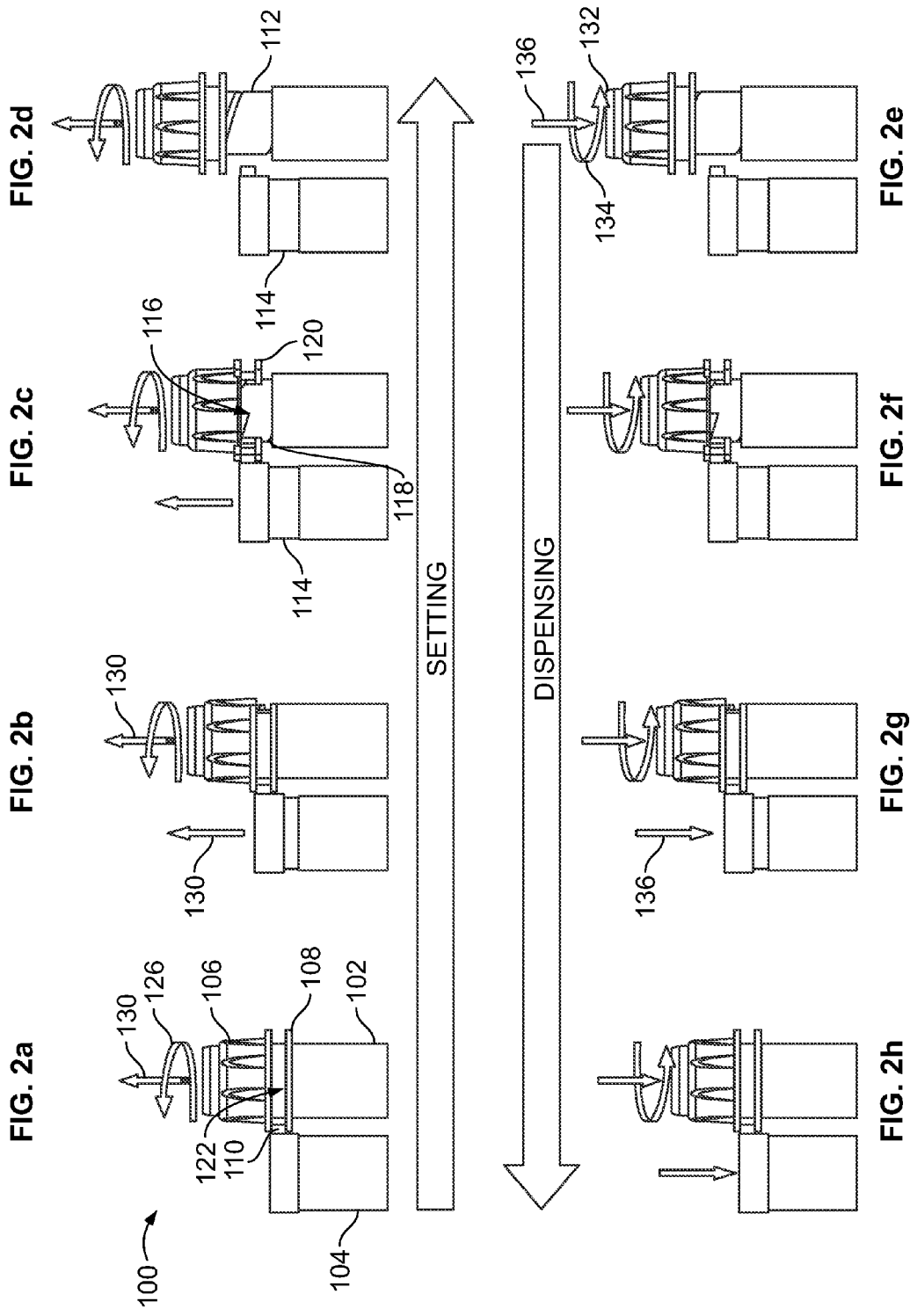
FIGS. 2a-h illustrates an example drug delivery device in accordance with an example of Applicants' disclosure at various phases of the operation of the device.
Figure 4:
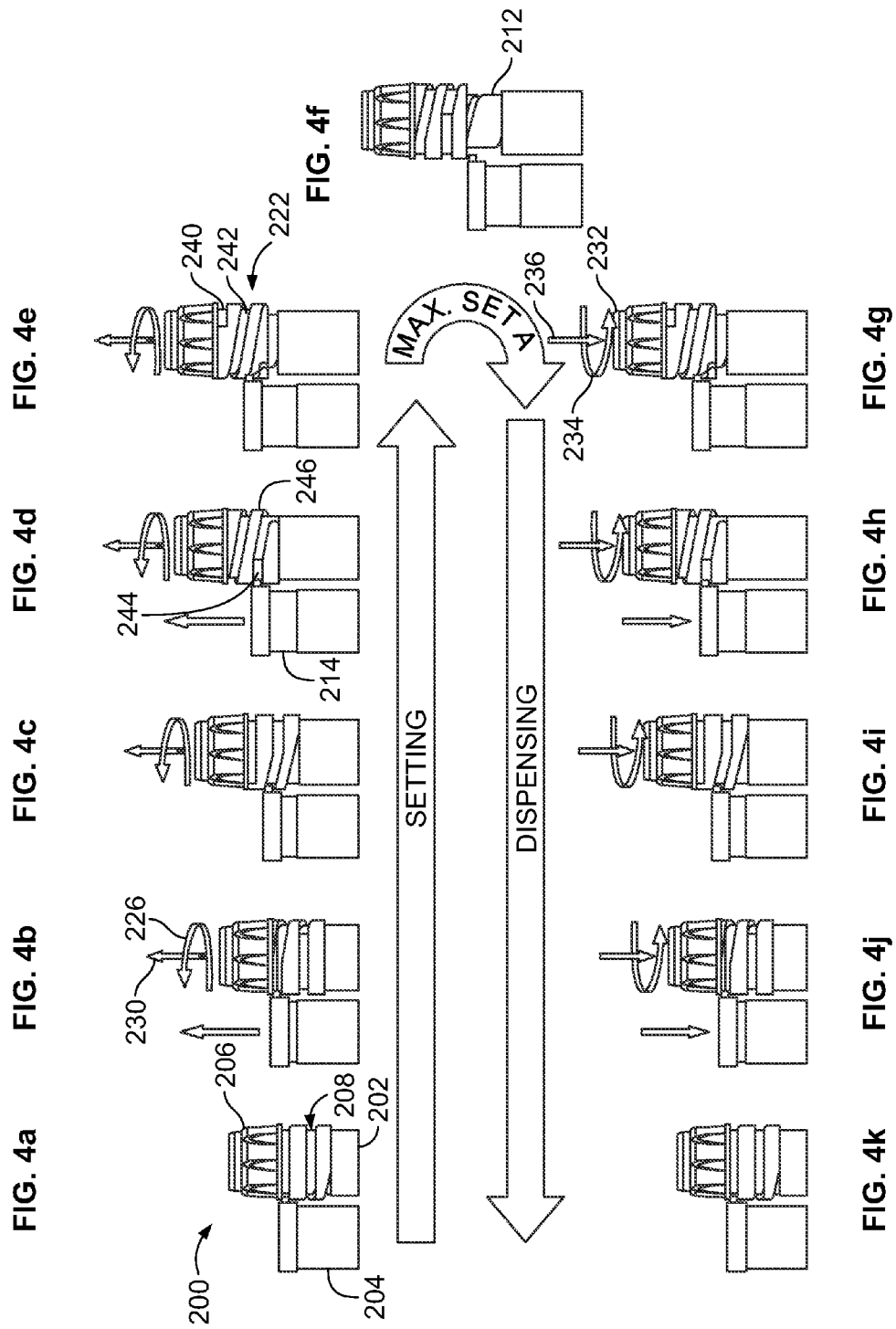
FIGS. 4a-k illustrates another example drug delivery device in accordance with an example of Applicants' disclosure at various phases of the operation of the device.
Figure 8:
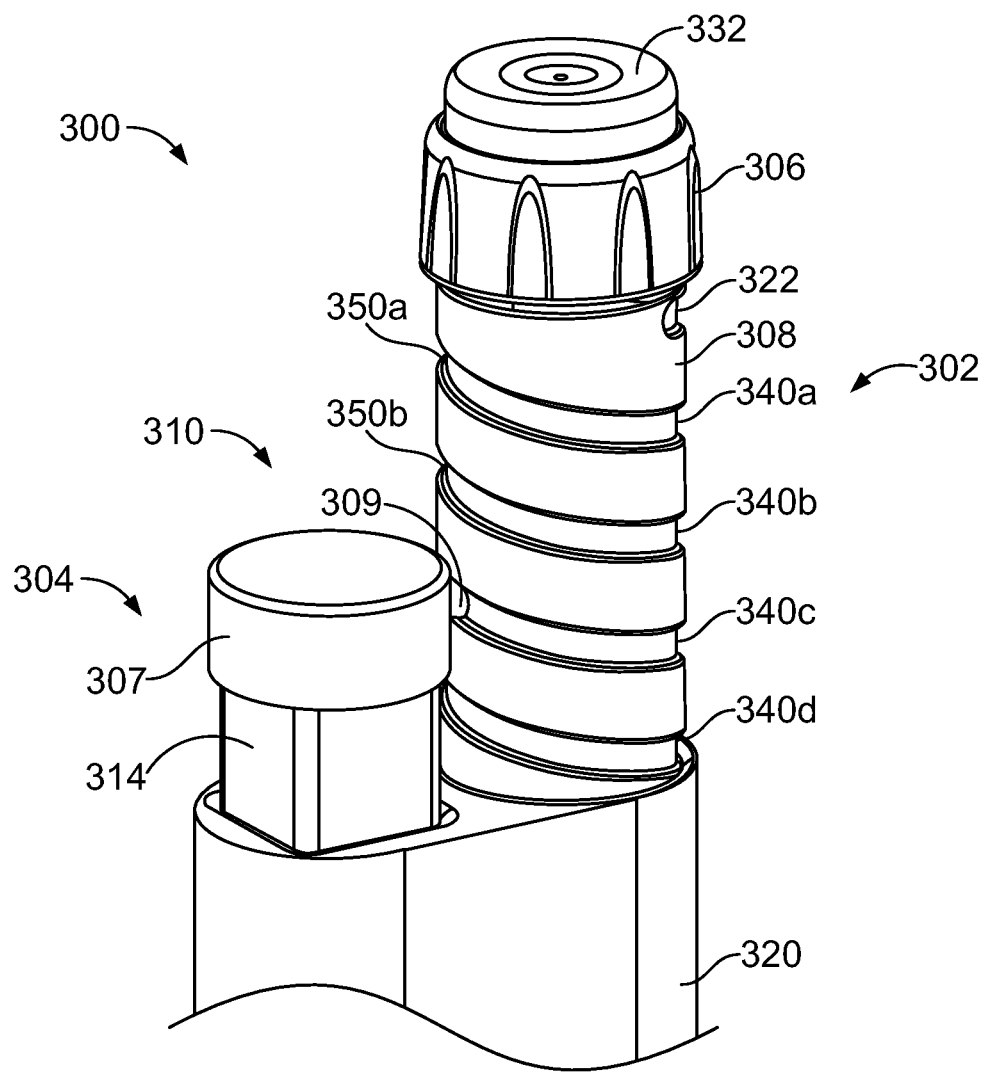
FIG. 8 illustrates an example drug delivery device in accordance with an example of Applicants' disclosure that is capable of dispensing at least one discrete, pulsed dose of a secondary medicament during the simultaneous delivery of the primary medicament.

A drug delivery device in accordance with Applicants' proposed concept may include a collar and a linkage component that mechanically link a variable dose setting mechanism and a fixed dose setting mechanism. FIGS. 2, 4, and 8 depict various examples of such a mechanical link. In general, a drug delivery device in accordance with Applicants' disclosure may comprise (i) a variable dose setting mechanism, wherein the variable dose setting mechanism is operably coupled to a primary reservoir holding a first medicament, (ii) a fixed dose setting mechanism, wherein the fixed dose setting mechanism comprises a fixed dose piston rod that is operably coupled to a secondary reservoir holding a second medicament, (iii) a single dose setter operably coupled to the variable dose setting mechanism, (iv) a collar disposed on the variable dose setting mechanism, and (v) a linkage component disposed on the fixed dose setting mechanism, wherein the linkage component is capable of engagement with the collar. In an example, the variable dose setting mechanism is a rotationally-set dose setting mechanism and the fixed dose setting mechanism is an axially-set dose setting mechanism. In one example, the fixed dose piston rod is operably coupled to a cartridge bung or stopper provided in the secondary reservoir holding the second medicament.

FIGS. 2*a-h* depict an example drug delivery device in accordance with an embodiment of Applicants' disclosure. In particular, FIGS. 2*a-h* depict a proximal end of drug delivery device 100 during setting and dispensing phases of operation. Drug delivery device 100 includes a first dose setting mechanism 102 and a second dose setting mechanism 104. The first dose setting mechanism 102 may be a variable dose setting mechanism that is operably connected to a first reservoir holding a first medicament, such as first reservoir 6 holding first medicament 1 shown in FIG. 1. First dose setting mechanism 102 may be a rotationally-set dose setting mechanism. Such dose setting mechanisms are generally known in the art. The second dose setting mechanism 104 may be a fixed dose setting mechanism that is operably connected to a second reservoir holding a second medicament, such as second reservoir 5 holding second medicament 2 shown in FIG. 1. Fixed dose mechanism 104 may be an axially-set dose setting mechanism (e.g., pull-to-set, push-to-dispense mechanism). Such dose setting mechanisms are generally known in the art.

The drug delivery device 100 also includes a single dose setter 106 that is operably coupled to the variable dose setting mechanism 102. A collar 108 is disposed on the variable dose setting mechanism 102 and a linkage component 110 is disposed on the fixed dose setting mechanism 104. In the example depicted, the linkage component is a pin. However, other types of components are possible, including but not limited to a flange element. The collar and pin arrangement between the dose setting mechanism 102, 104 may result in a desired dose profile, such as a profile that comprises a variable dose of the first medicament 1 and a delayed, fixed dose of the second medicament 2, such as that shown in FIG. 3.

The collar 108 may be disposed on the variable dose setting mechanism 102 at various locations. For example, in the example of FIG. 2, the collar 108 is attached to a dial sleeve 112. However, in another example, the collar 108 could be disposed on the dose setter 106 itself, such as on the distal end of the dose setter 106. As depicted, the collar 108 may be a ring-shaped collar having a gap 116 (see FIGS. 2*c* and 2*f*) between a first end 118 of the collar and the second end 120 of the collar. The ring shape may generally be any suitable ring shape, such as a circular ring shape, an oval ring shape, or generally any polygonal ring shape. The collar 108 may also comprise a groove 122, and the linkage component 110 may be slidably engageable with the groove 122. The pin may be fixed to a moving rack 114 of the axially-set fixed dose setting mechanism 104. The pin 110 interfaces with the collar 108 such that when the collar 108 is rotated and moved in the proximal direction by the setting action, the pin 110 (and consequently the moving rack 114) is pulled in the proximal direction, thus setting the fixed dose setting mechanism 104.

The setting and dispensing phases are depicted in detail in FIGS. 2*a-h*. In particular, FIGS. 2*a*-2*d* depict various points during setting of the drug delivery device 100, and FIGS. 2*e-h* depict various points during dispense. As shown in FIG. 2*a*, when a user begins to rotate the dose setter 106 in rotational direction 126, the pin 110 rides within the collar groove 122. Although depicted here as being disposed in the collar groove 122 in the starting position (i.e., pre-set position), in other examples, the pin may not be engaged with the collar groove 122 until after dose setting has begun.

FIG. 2b depicts further setting of the variable dose setting mechanism 102. As the dose setter 106 (and therefore the collar 108) is rotated, the dial sleeve 112 rises in proximal direction 130 to set the variable dose of the first medicament. The pin 110 is also pulled up in proximal direction 130, and this action begins to set the fixed dose of the second medicament 2.

When the pin is lifted to the set point of the fixed dose setting mechanism 104, the gap 116 in the collar 108 allows the pin to disengage from the groove 122. The set point of fixed dose setting mechanism 104 is shown in FIG. 2c. When the second medicament 2 is fully set, the collar rotates past the pin 110 to allow for further setting of the first medicament 1, as shown in FIG. 2d. In other words, higher doses of the first medicament 1 may be set after the pin disengages from the collar after the fixed dose of the second medicament 2 is set.

FIG. 2e depicts the beginning of the dispense process. In particular, the dispense process may begin when a user pushes dose button 132. This action causes the dose setter 106 (and therefore the collar 108) to rotate in rotational direction 134, which in turn causes movement of the dose setter 106 in distal direction 136. This movement in distal direction 136 may begin the dispense of the first medicament 1. As shown in FIG. 2f, as the dose setter 106 and collar 108 rotate back down during dispense of the first medicament, the collar groove 122 realigns with the pin 110 and thus reengages with the pin 110. Further movement in the rotational direction 134 and distal direction 136 causes the collar 108 to push against the pin 110 and move the pin in the distal direction 136 as the pin moves through groove 122, as shown in FIG. 2g. When the dose setter 106 is fully depressed back to its starting position (i.e., pre-set position), as shown in FIG. 2h, both the first medicament 1 and the second medicament 2 are fully dispensed.

Figure 3:
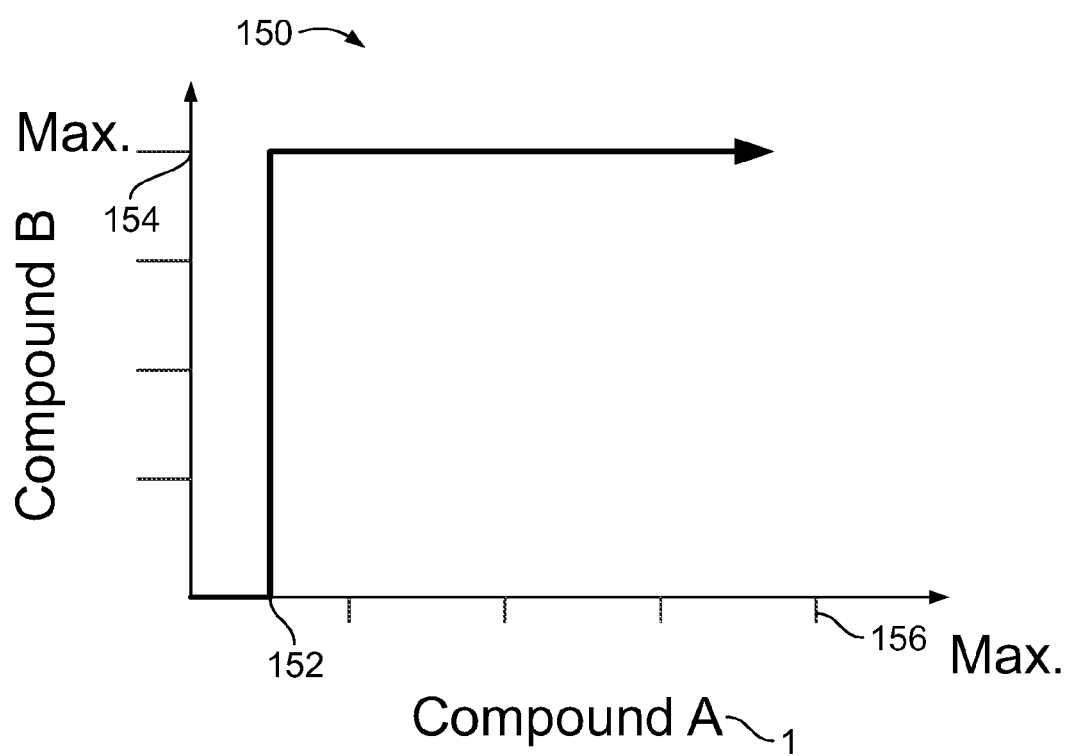
FIG. 3 illustrates an example possible dose profile achievable with the drug delivery device illustrated in FIG. 2.

Drug delivery device 100 may beneficially deliver a therapeutic dose profile that involves delivering a variable dose of a first medicament and delivering a fixed dose of a second medicament after a minimum dose of the first medicament is set. An example of such a profile is shown in FIG. 3. As seen in FIG. 3, profile 150 involves a fixed dose 154 of the second medicament 2 being set after a minimum variable dose 152 of the first medicament 1 is set. After the fixed dose 154 is set, the variable dose may be dialed further, such as up to a maximum dose 156.

For low dose settings of the first medicament 1 below the minimum threshold 152, the fixed dose setting mechanism does not reach its set point. In some examples, if this is the case, none of the second medicament would be dispensed. That is, the fixed dose setting mechanism 104 may be configured to only dispense medicament after a full fixed dose is set. Should a dose less than the full dose be set, the fixed dose setting mechanism may simply be configured to return to its starting position without dispensing a dose. Thus, the drug delivery device 100 beneficially may allow for priming of the device using just the first medicament 1. The device 100 may be particularly advantageous for examples where the second medicament 2 is particularly expensive compared to the first medicament 1. Since the fixed dose of the second medicament may not be set until a minimum dose of the first medicament 1 is set, the user may dial a priming dose (e.g., a dose less than dose 152) and prime solely with the first medicament.

A second example drug delivery device is shown in FIGS. 4a-k. In particular, FIGS. 4a-k depict a proximal end of drug delivery device 200 during setting and dispensing phases of operation. This drug delivery device 200 is similar in many respects to drug delivery device 100. For instance, drug delivery device 200 includes a first dose setting mechanism 202 operably connected to a primary reservoir holding a first medicament, such as first reservoir 6 holding first medicament 1. Drug delivery device 200 also includes a second dose setting mechanism 204 operably connected to a secondary reservoir holding a second medicament, such as second reservoir 5 holding second medicament 2. The drug delivery device 200 further includes a single dose setter 206 that is operably coupled to the variable dose setting mechanism 202. A collar 208 is disposed on the variable dose setting mechanism 202 and a linkage component 210 is disposed on the fixed dose setting mechanism 204. The linkage component 210 comprises a pin 209 and a pin cap 207.

These various components are generally the same as or similar to the corresponding components of drug delivery device 100; however, drug delivery device 200 has a modified collar 208 and a modified fixed dose setting mechanism 204. This modified collar 208 allows for achieving a modified therapeutic dose profile. Further, the modified fixed dose setting mechanism 204 allows for setting of a fixed dose that follows a stepped fixed dose profile. In other words, the fixed dose setting mechanism allows for the settable fixed dose to increase in increments based on the value of the dialed variable dose. Similar to the fixed dose mechanism 104, fixed dose setting mechanism 204 may be an axially-set fixed dose setting mechanism. As is generally known in the art, such devices may contain ratchet features to facilitate setting of a dose of medicament. In this case, additional ratchet features may be required to allow for half dose setting as well as full dose setting (described below). In a particular example, approximately 28 ratchet steps would be used; however, this number of ratchet steps can vary as needed. For example, having ratchet steps in multiples of 7 may be potentially beneficial as it relates directly to weeks, making planning for replacement prescriptions etc easier for a user. In one exemplary arrangement, Applicants' device may be configured such that the device has an additional, setting that facilitates priming. After this prime dose, the device is capable of delivering 14 further, 'complete' doses.

Figure 5:
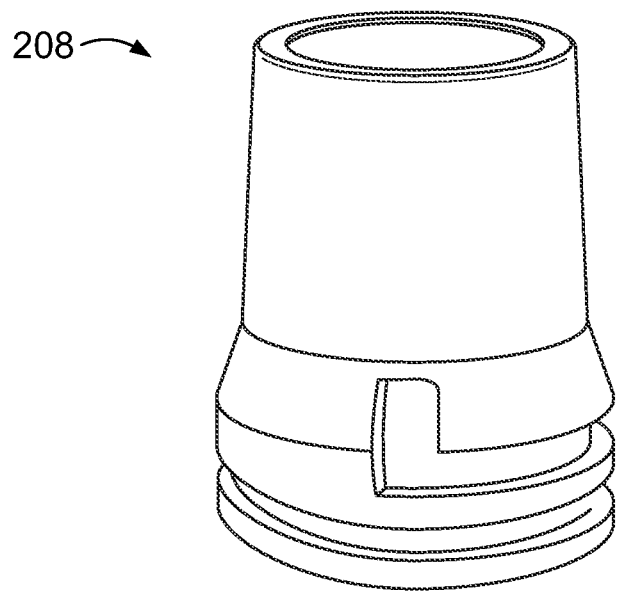
FIG. 5 illustrates a perspective view of collar of FIGS. 4a-c, where the collar is shown not yet disposed on a drug delivery device.

Specifically, the modified collar includes a groove having a plurality of sections. For example, the collar may comprise a groove having at least a first section that is a generally flat section and a second section that comprises a helical section. For instance, the collar 208 depicted in FIGS. 4a-k has a groove 222 that comprises four different sections. In particular, groove 222 has a first section 240, a second section 242, a third section 244, and a fourth section 246. The first section 240 and third section 244 are generally flat sections, whereas the second section 242 and fourth section 246 are helical sections. FIG. 5 illustrates a perspective view of collar 208, where the collar is shown not yet disposed on drug delivery device 200.

A collar such as collar 208 may beneficially achieve a stepped fixed dose profile. In particular, drug delivery device 200 may beneficially deliver a therapeutic dose profile that involves delivering a variable dose of a first medicament and delivering a stepped, fixed dose of a second medicament. For instance, a first fixed dose amount of the second medicament 2 may be set after a first minimum dose of the first medicament 1 is set, and a second fixed dose amount of the second medicament 2 may be set after a second minimum dose of the first medicament 1 is set. In an example, the collar 208 and fixed dose setting mechanism 204 may be configured to (i) set a half fixed dose of the second medicament 2 upon setting of a first minimum variable dose of the first medicament 1 and (ii) set a full fixed dose of the second medicament 2 upon setting of a second threshold dose of the first medicament 1. Such a profile is advantageous for certain therapies where it is beneficial for the dose of the second medicament 2 to increase in fixed stepped increments as the corresponding dose of the first medicament 1 increases. Each of these stepped increases only occurs once a specific predefined threshold dose of the first medicament 1 has been exceeded.

Figure 6A:
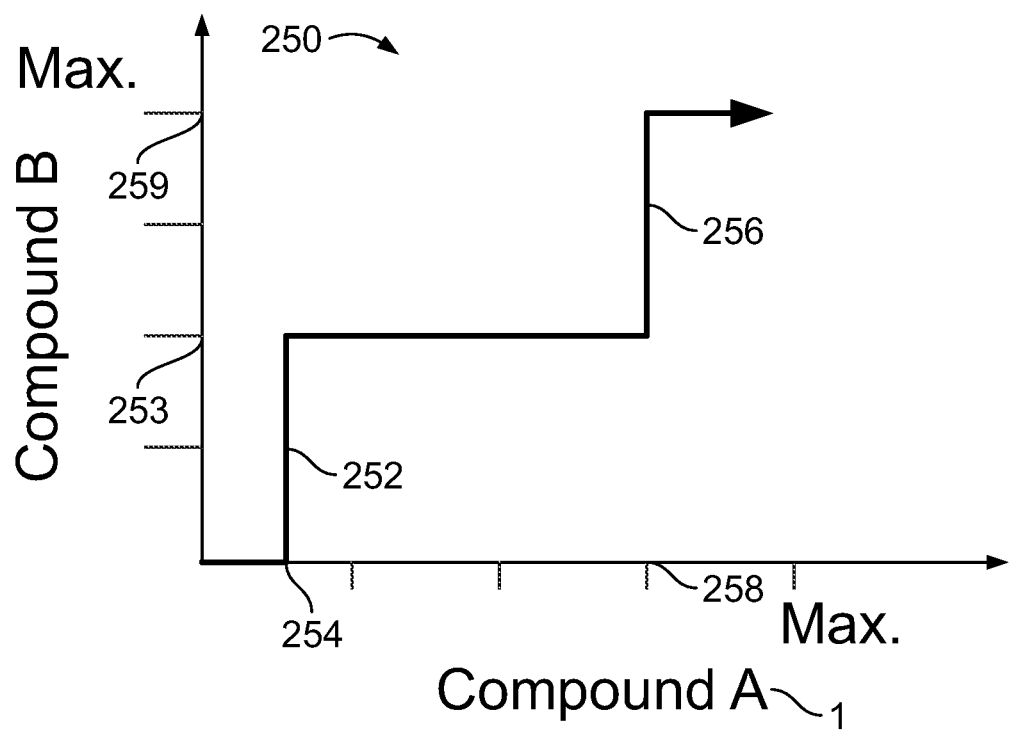

Various examples of such a stepped, fixed dose profile are shown in FIG. 6*a-c*. In the profile 250 shown in FIG. 6*a*, the first step 252 occurs when a threshold dose 254 of the first medicament 1 is set. The first step 252 results in a dose 253 of the second medicament 2 being set. In this example, the dose 253 is a half dose of the second medicament 2. However, it should be understood that the dose 253 could be any desired percentage of the second medicament 2. For example, this could be achieved by having non-uniform pitches (i.e., ratchet pitch for step 1 252 being different fro that pitch of step 2 256. The second step 256 occurs when a threshold dose 258 of the first medicament 1 is set. The second step 256 results in a dose 259 of the second medicament 2 being set. In this example, the dose 259 is a full (e.g., maximum) dose of the second medicament 2. However, it should be understood that the dose 259 could be any desired percentage of the second medicament 2. In this example, after the full dose 259 is set, the user may continue to set a higher dose of the first medicament 1. In addition, although only two steps are shown in this example dose profile, more steps are possible.

An example advantage of a drug delivery device such as drug delivery device 200 is the ability to define where the half and full set points (or any desired percentage) of the second medicament 2 occur relative to the setting of the first medicament 1. Potentially several variations of the drug delivery device could be manufactured and user prescribed to fit a variety of specific user needs. For example, a user who may typically use a high amount of the first medicament 1 may wish to split their dose (e.g., set and inject half a dose in one location and then set and inject the second half dose in another location) or may be required to split their dose to avoid injecting a high volume of medicament in a single location (which can, for example, cause discomfort). Such a user may benefit from the second threshold of the first medicament 1 (which determines when the full dose of the second medicament is set) being at a much higher point than their half dose of the first medicament, for example, in order to reduce the risk of overdosing the secondary medicament during split dose scenarios. An example of such a dose profile is shown in FIG. 6*b*. Dose profile 260 involves (i) setting a half dose 262 of the second medicament 2 upon setting of a variable dose 264 of the first medicament 1 and (ii) setting of the full dose 266 of the second medicament 2 upon setting of a variable dose 268 of the first medicament 1. As can be seen, the second threshold variable dose 268 is close to the maximum possible settable dose of the first medicament 1. Thus, a user who wishes to split injections may dial a half dose of the first medicament 1 (and deliver a half fixed dose of the second medicament with each half of their dose of the first medicament).

In another example, a user who may typically use a small amount of the first medicament 1 may ideally obtain their full dose of the second medicament 2 at their relatively low dose of the first medicament 1. The user may thus avoid the need for injecting more of the first medicament 1 than desired to obtain a full fixed dose of the second medicament 2. An example of such a dose profile is shown in FIG. 6*c*. Dose profile 270 involves (i) setting a half dose 272 of the second medicament upon setting of a low variable dose 274 of the first medicament and (ii) setting of the full dose 276 of the second medicament upon setting of a low variable dose 278 of the first medicament. Thus, a user does not have to dial nearly as high of a dose of the first medicament 1 to deliver a full fixed dose as in the example shown in FIG. 6*b*.

The setting and dispensing phases of drug delivery device 200 are depicted in detail in FIGS. 4*a-k*. In particular, FIGS. 4*a*-4*e* each depict various points during setting of the drug delivery device 200, and FIGS. 4*f-k* each depict various points during dispense. As shown in FIG. 4*a*, when a user begins to rotate the dose setter 206 in rotational direction 226, the pin 209 of pin cap 207 is in the collar groove 222 and, in particular, in the flat section 240 of the groove. As the dose setter 206 (and therefore the collar 208) is rotated, the dial sleeve 212 rises in proximal direction 230 to set the variable dose of the first medicament 1 and also forces the pin 209 to travel through the flat section 240. The pin may be fixed to a moving rack 214 of the axially-set fixed dose setting mechanism 204. The pin interfaces with the collar such that when the collar is rotated and moved in the proximal direction by the setting action, the pin (and consequently the moving rack) is pulled in the proximal direction, thus setting the fixed dose setting mechanism 204. With reference to FIG. 4*b*, as the pin travels through flat section 240, the fixed dose setting mechanism 204 also moves axially in proximal direction 230, thus beginning to set the fixed dose of the second medicament. This may set the half dose 253 of the second medicament 2 (see FIG. 6*a*).

As shown in FIG. 4*c*, after a given amount of movement in the proximal direction 230, the pin 209 enters the second/helical section 242. In this example, the helical section 242 is the same pitch as the dial sleeve of the variable dose setting mechanism and therefore results in the collar 208 rotating past the pin and not loading the fixed dose setting mechanism 204. In other words, as the pin 209 moves through the helical section 242, the fixed dose setting mechanism 204 does not move in the proximal direction 230.

After a given amount of rotation, the pin 209 enters the third/flat section 244, as shown in FIG. 4*d*. Further rotation then forces the pin 209 to travel through the flat section 244. With reference to FIG. 4*e*, as the pin travels through flat section 244, the fixed dose setting mechanism 204 also moves axially in proximal direction 230, thus setting the fixed dose of the second medicament 2. This may, for example, be the action that sets the full dose 259 of the second medicament (see FIG. 6*a*).

After the full fixed dose of the second medicament is set, the dose setter 206 may be rotated further to set a higher dose of the first medicament 1. In particular, when the pin 209 travels through the third, flat section 244, the pin then enters the fourth/helical section 246. In this section, the helical section 246 is the same pitch as the dial sleeve of the variable dose setting mechanism and so results in the collar 208 rotating past the pin and not loading the fixed dose setting mechanism. The pin may then exit the fourth, helical section 246 and the user can continue to set a higher dose of the first medicament, if desired.

In another example, the collar 208 may not include a fourth helical section. Rather, the collar may simply end at the third, flat section 244, and when the pin 209 exits this flat section, the dose setter could continue to be rotated to set a higher dose of the first medicament, if desired.

After setting the desired dose of the first medicament, the user may dispense the medicament. FIG. 4*g* depicts the beginning of the dispense process. In particular, the dispense process may begin when a user pushes dose button 232. This action causes the dose setter 206 (and therefore the collar 208) to rotate in rotational direction 234, which in turn causes movement of the dose setter 206 in distal direction 236. This movement in distal direction 236 may begin dispense of the first medicament 1. As shown in FIGS. 4g-h, as the dose setter 206 and collar 208 rotate back down during dispense of the first medicament 1, the pin 209 realigns with the flat section 244. Further movement in the rotational direction 234 and thus distal direction 236 causes the collar 208 to push against the pin 210 and move the pin in the distal direction 236 as the pin moves through the flat section 244. This action begins dispense of the second medicament 2. In the example where this flat section 244 increases the dose from a half dose to a full dose, half of the dose of the second medicament 2 will be dispensed as the pin travels through the flat section 244.

Further rotation forces the pin 210 to move through the helical section 242. Since the pitch matches that of the dial sleeve 212, the helical section winds back past the pin 209, and this action does not cause axial movement of the fixed dose setting mechanism in distal direction 236. However, the pin 209 then enters the flat section 240, as shown in FIGS. 4i-j, and this forces continued dispense of the second medicament 2. In the example where this flat section 240 sets the first half dose, that half of the dose of the second medicament will be dispensed as the pin travels through the flat section 240. When the dose setter 206 is fully depressed back to its starting position (i.e., pre-set position), as shown in FIG. 4k, both the first medicament 1 and the second medicament 2 are fully dispensed.

Beneficially, the groove sections can be modified in order to achieve a desired dose profile. For example, the groove may have more flat sections and more helical sections, and thus may result in more steps in the stepped, fixed dose profile. For instance, the groove sections could be designed such that the drug delivery device is capable of setting a ¼ dose, ½ dose, ¾ dose, and a full dose.

As another example, rather than having a flat section, the collar 208 may comprise a groove having (i) a first section that is a first helical section having a first pitch and (ii) a second section that is a second helical section having a second pitch different from the first pitch.

In yet another example, a drug delivery device having a collar may be configured to deliver medicament according to a dose profile that involves delivering a fixed ratio, a first fixed dose, an offset fixed ratio, and a second fixed dose. Similar to the example discussed above with respect to FIG. 4, a particular advantage of such a dose profile is the ability to define where the half and full set points (or any desired percentage) of the second medicament occur relative to the setting of the first medicament. Potentially several variations of the drug delivery device could be manufactured and user prescribed to fit a variety of specific user needs. For example, a user who may typically use a high amount of the first medicament may wish to split their dose (e.g., set and inject half a dose in one location and then set and inject the second half dose in another location) to avoid injecting a high volume of medicament in a single location (which can cause discomfort). Such a user may benefit from the second minimum threshold of the first medicament (which determines when the full dose of the second medicament is set) being at a higher point than their half dose of the first medicament.

An example of a dose profile that involves a fixed ratio, a first fixed dose, an offset fixed ratio, and a second fixed dose is shown in FIG. 7a. Dose profile 280 involves a fixed ratio portion 282, a first fixed dose portion 284 of the second medicament 2, an offset fixed ratio portion 286, and a second fixed dose portion 288 of the second medicament 2. Another example of a dose profile that involves a fixed ratio, a first fixed dose, an offset fixed ratio, and a second fixed dose is shown in FIG. 7b. Dose profile 290 involves a fixed ratio portion 292, a first fixed dose portion 294, an offset fixed ratio portion 296, and a second fixed dose portion 298. Similar to the profile described with respect to FIG. 6c, the example profile 280 may be useful for a low volume of first medicament user. Further, the example profile 290 may be useful for a high volume user of the first medicament.

FIG. 8 depicts an example drug delivery device 300 that may be used to achieve a pulsed dose profile. Preferably, the drug delivery device 300 comprises an outer housing 320 containing a first reservoir 5 containing a first medicament and a second reservoir 6 containing a second medicament, similar to the reservoir illustrated in FIG. 1. The drug delivery device 300 further comprises a variable dose setting mechanism 302 operably coupled to the primary reservoir 5 and a fixed dose setting mechanism 304 operably coupled to the secondary reservoir 6.

A pulsed dose profile achieved by drug delivery device 300 could comprise a pulsed dose profile of a second medicament 2 contained within a second reservoir or cartridge 6. For instance, in such a device 300, a first fixed dose amount of the second medicament 2 may be set after a first minimum dose or first threshold dose of the first medicament 1 is set. Similarly, a second fixed dose or a second amount of the second medicament 2 (i.e., the second fixed dose being greater than the first fixed dose) may be set after a second minimum dose or second threshold dose of the first medicament 1 is set. In an example, the collar 308 and fixed dose setting mechanism 304 may be configured to (i) set a first fixed dose (or proportion of a dose) of the second medicament 2 upon setting of a first minimum variable dose of the first medicament 1, (ii) set a second fixed dose (or proportion of a dose) of the second medicament 2 upon setting of a second threshold dose of the first medicament 1, (iii) administer the set fixed dose of the second medicament 2 using a plurality of discrete pulses. The first fixed dose could comprise a certain percentage of a target fixed dose and the second fixed dose could comprise the balance of the target fixed dose. As just one example, assume that the target fixed dose comprises 100 Units of the second medicament. With such a target dose, the first fixed dose could comprise 40% of a target fixed dose (i.e., 40 Units) and the second fixed dose could comprise 60% or the remaining balance (i.e., 60 Units) of the target fixed dose (i.e., 100 Units). As those of skill in the art will recognize, alternative fixed dose and target dose arrangements may also be used.

Such a profile can be advantageous for certain therapies where it is beneficial for the dose of the second medicament 2 to increase in fixed stepped increments as the corresponding dose of the first medicament 1 increases. In one preferred arrangement, a stepped increase occurs after a specific predefined threshold dose of the first medicament 1 has been exceeded. Moreover, depending on the configuration of the variable dose setting mechanism 302 and the fixed dose setting mechanism 304 (i.e., particularly the collar 308 and the fixed dose piston rod 316), the pulsed nature of administration can be modified.

Figure 12:
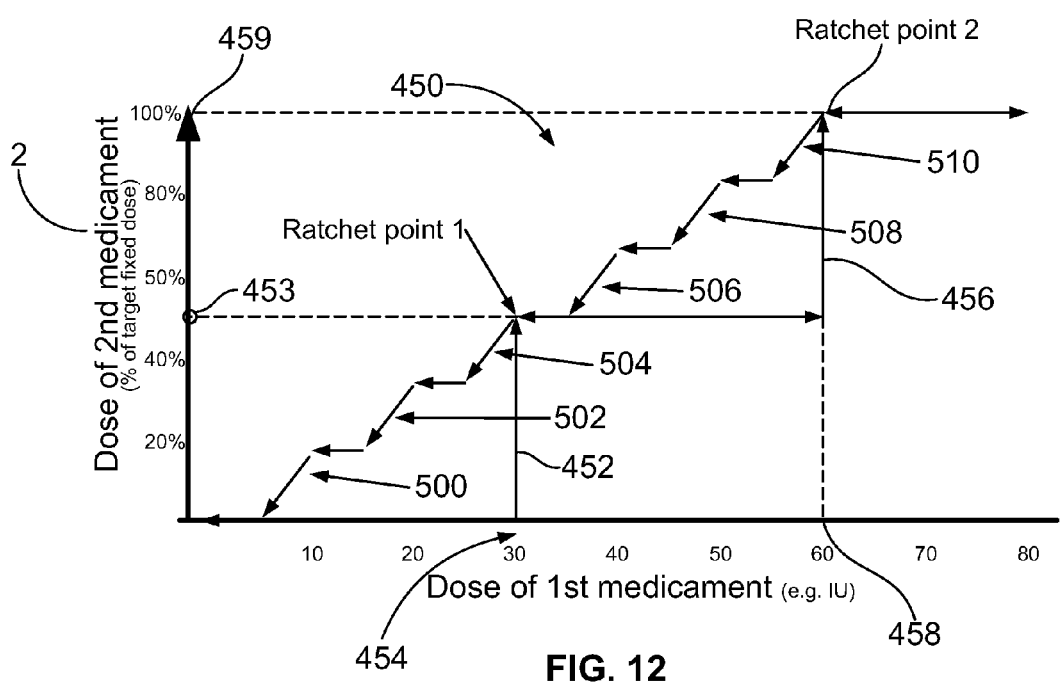

One example of such a stepped, fixed dose profile that can be achieved by the drug delivery device 300 is the profile 450 illustrated in FIG. 12. In the profile 450 shown in FIG. 12, the first step 452 occurs when a minimum dose of a first threshold dose 454 of the first medicament 1 is set by way of a variable dose setting mechanism 302. The first step 452 results in a dose 453 of the second medicament 2 being set. In this example, the dose of the first medicament 1 is 30 Units and the dose 453 is a half dose of the targeted fixed dose 459 of the second medicament 2. As will be explained in greater detail below, this first step 452 occurs when the fixed dose setting mechanism 304 (i.e., the fixed dose piston rod 316 of the dose setting mechanism 304) moves a certain predefined distance in the proximal direction. However, it should be understood that the first fixed dose 453 could be any desired percentage of the second medicament 2. For example, and as explained in greater detail below, this could be achieved by having non-uniform distances between adjacent ratchet element sets provided along the surface of the piston rod 316.

If the combined first and second medicament dose would be administered at this point in the profile 450 designated as "Ratchet point 1," a dose comprising 50% of the target fixed dose 459 of the second medicament 2 would be administered by way of three pulses: Pulse C 504, Pulse B 502, and Pulse A 500. This point has been designated as "Ratchet point 1" in profile 450 since this defines the minimum required dose that needs to be set for the first medicament 1 in order for the movable rack of the fixed dose setting mechanism 304 to move proximally to reach the first ratchet element set provided on the piston rod. The set dose 454 of the first medicament 1, a 30 Unit dose of the first medicament 1, would be administered continuously during this dose administration step.

The profile 450 further comprises a second step 456. The second step 456 occurs when a second threshold dose 458 (e.g., 60 Units in the embodiment provided) of the first medicament 1 is set. The second step 456 results in a second part or the remaining portion of the target dose 459 of the second medicament 2 being set. In this example, the target dose 459 is a full dose (e.g., maximum or target dose) of the second medicament 2. However, it should be understood that the dose 459 could be any desired percentage of the second medicament 2. This point has been designated as "Ratchet point 2" in profile 450 since this point defines a second minimum dose that is required that needs to be set for the first medicament 1 in order for the movable rack of the fixed dose setting mechanism 304 to move proximally and thereby reach a second ratchet element set provided along the outer surface of the fixed dose piston rod.

Once a user sets a 60 Unit dose of the first medicament, the combined dose would comprise the targeted dose 459 comprising 100% of the second medicament and 60 Units of the first medicament 1. Administering this target fixed dose 459 would be administered by way of six sequential pulses: Pulse F 510, Pulse E 508, Pulse D 506, Pulse C 504, Pulse B 502, and Pulse A 500. The set dose 458 of the first medicament 1, a 60 Unit dose of the first medicament 1, would be administered continuously during the entire dose administration process. To administer six pulses of the second medicament during dose administration, a groove 322 of the collar 308 would comprise at least six threaded sections.

In this example, after the full dose 459 is set, the user may continue to set a higher dose of the first medicament 1. In addition, although only two steps 452, 456 are shown in this example dose profile 450, more steps are possible.

An example advantage of Applicants' drug delivery device, such as the drug delivery device 300 illustrated in FIG. 8, is the ability to define where the half and full set points (or any desired percentage) of the second medicament 2 occur relative to the setting of the first medicament 1 and to administer the second medicament by way of one or more discrete pulses, such as pulses 501, 508, 506, 504, 502 and 500 illustrated in profile 450.

Potentially several variations of the drug delivery device 300 could be manufactured and user prescribed to fit a variety of specific user needs. For example, a user who may typically use a high amount of the first medicament 1 may wish to split their dose (e.g., set and inject half a dose in one location and then set and inject the second half dose in another location) or may be required to split their dose to avoid injecting a high volume of medicament in a single location (which can, for example, cause discomfort). Such a user may benefit from the second threshold of the first medicament 1 (which determines when the full dose of the second medicament is set) being at a much higher point than their half dose of the first medicament, for example, in order to reduce the risk of overdosing the secondary medicament during split dose scenarios.

Figure 9A:
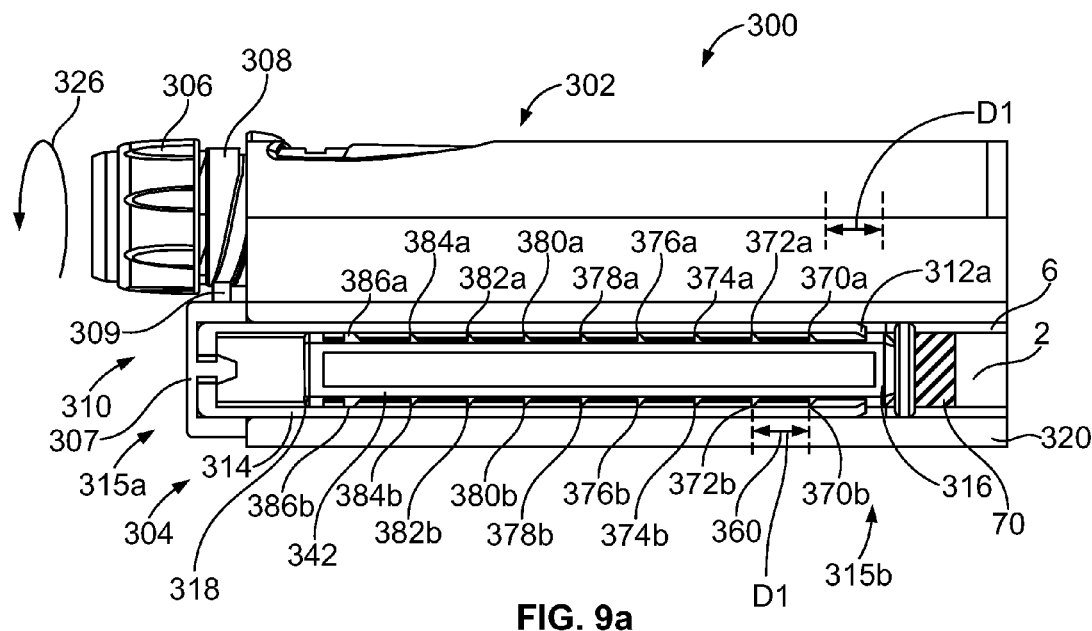
FIGS. 9a-h illustrates the drug delivery device illustrated in FIG. 8 at various phases of dose dialing.
Figure 11:
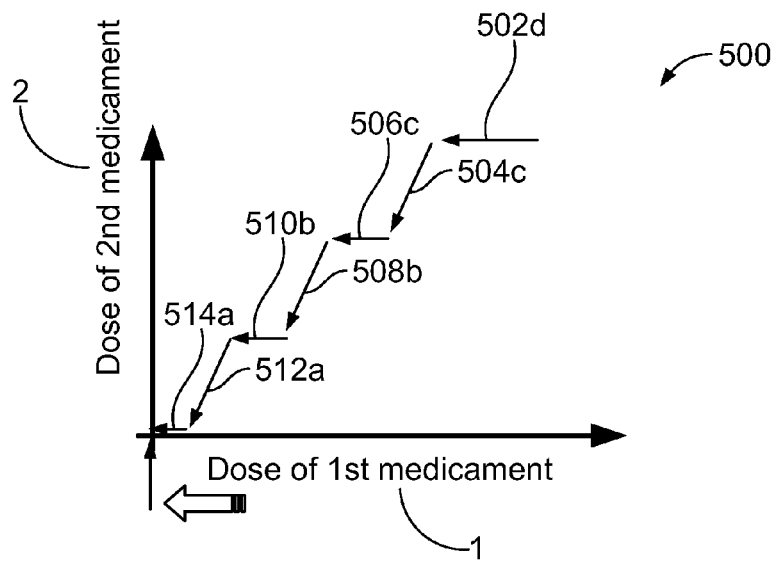
FIGS. 11-12 illustrate example possible dose profiles achievable with the drug delivery device illustrated in FIG. 8.

FIG. 8 depicts an example drug delivery device 300 that may be used to achieve a pulsed dose profile, such as the pulsed dose profile 450 illustrated in FIG. 11. FIG. 9*a* illustrates a proximal end portion of the drug delivery device 300 with the fixed dose setting mechanism illustrated in cross section view.

Referring now to FIGS. 8 and 9*a*, drug delivery device 300 is similar in certain respects to drug delivery device 200. For example, the drug delivery device 300 comprises a variable dose setting mechanism 302 and a fixed dose setting mechanism 304. The various components making up these mechanisms 302, 304 are generally the same as or similar to the corresponding components of drug delivery device 200. For example, the variable dose setting mechanism 302 comprises a dose button 332, a single dose setter 306, and a collar 308 comprising a groove 322. Groove 322 may comprise one or more flat thread sections and one or more helical thread sections, similar to the groove 222 described above. The variable dose setting mechanism also comprises a dose dial sleeve that allows the variable dose setting mechanism to translate in the proximal direction during dose setting and to translate in the distal direction during dose dispense.

However, as compared to the device 200 illustrated in FIGS. 4*a-g*, drug delivery device 300 comprises a modified collar 308 and a modified fixed dose setting mechanism 304. This modified collar 308 allows the drug delivery device 300 to achieve a modified therapeutic dose profile. As just one example, in a preferred arrangement, this modified therapeutic dose profile comprises a combination dose containing a variable dose of the first medicament 1 and a fixed dose of the second medicament 2 where this second medicament 2 is administered via at least one discrete pulse of the second medicament 2.

The modified fixed dose setting mechanism 304 comprises a modified moving rack 314 along with a fixed dose piston rod arrangement 316. In this arrangement, and as illustrated in FIG. 9*a*, the moving rack 314 extends from a proximal end 315*a* to a distal end 315*b* within the outer housing 320 of the drug delivery device 300. At the proximal end 315*a* of the moving rack 314, a linkage component 310 is rigidly affixed. This linkage component 310 comprises a pin cap 307 comprising a radially extending pin 309. In one preferred arrangement, the pin cap 307 and the pin 309 comprise a unitary component.

At its distal end 315*b*, the moving rack 314 comprises a set of one way ratchet arms 312*a,b*. In addition, the modified fixed dose setting mechanism 304 further comprises a fixed dose piston rod 316. This fixed dose piston rod 316 comprises a plurality of ratchet element sets 370 *a,b;* 372 *a,b;* 374 *a,b;* 376 *a,b;* 378 *a,b;* 380 *a,b;* 382 *a,b;* 384 *a,b;* and 386 *a,b* situated along an outer surface 342 of the rod 316. As illustrated, these ratchet elements sets 370*a,b*-386*a,b* are positioned at predetermined positions along the outer surface 342 of the piston rod 316. As will be explained in greater detail below, as the fixed dose setting mechanism 304 and hence the moving rack 314 is moved in a proximal direction 330 a certain predefined distance during certain dose setting steps, the one way ratchet arms 312 *a,b* of the movable rack 314 will pulled in the proximal direction 330. If the one way ratchet arms 312 *a,b* are moved in the proximal direction 330*a* sufficient distance, these ratchet arms 312 a,b will eventually ride over a ratchet element set so as to set a predetermined, fixed dose.

As can be seen from FIG. 9a, the spacing between adjacent ratchet element sets 370 a,b-386 a,b along the fixed dose piston rod is constant, but need not be constant. For example, in an alternative fixed dose piston rod arrangement, the spacing between adjacent ratchet element sets may vary.

It is this ratchet element set spacing and its relation to the amount of axial movement of the pin 310 and pin sleeve 307 of collar 308 during each flat thread section on the collar during dialing and dispense that determines a number of important drug delivery device design parameters. For example, the distance D1 360 between the first ratchet element set 370 a,b and the distal end 318 of the fixed dose piston rod 316 defines the first predetermined fixed dose. Similarly, the distance D2 between the first ratchet element set 370 a,b and the second ratchet element set 372 a,b determines (in conjunction with D1) the minimum dose of the first medicament that needs to be dialed before the second predetermined fixed dose of the secondary medicament is set. In addition, the distances D1 and D2 along with the configuration of groove 322 determine the number of discrete pulses of the secondary medicament 2 that can be delivered during a dispense action (i.e., after one or more of the ratchet element sets have been overcome by the one way ratchet arms 312 a,b).

In this case, the fixed dose piston rod 316 comprises nine ratchet element sets; however, this number of ratchet element sets can vary as needed. For example, having ratchet element sets in multiples of 7 may be potentially beneficial as it relates directly to the days in a week, making planning for replacement prescriptions easier for a target user having a once a day dosing regime. As those of skill will recognize, alternative ratchet element set configurations are possible.

The various ratchet element sets 370 a,b-386 a,b define a plurality of target doses that may be administered by way of the fixed dosing mechanism 304. Used in combination with the groove 322 provided on the modified collar arrangement 308, these ratchet sets 370 a,b-386 a,b work in cooperation with the one way ratchet arms 312 a,b so as to allow for administering a fixed dose by way of a plurality of incremental pulses. In other words, the fixed dose setting mechanism 304 allows for the non user-settable fixed dose to increase in increments based on the value of the dialed variable dose of the first medicament 1 and also allows this settable fixed dose to be administered by way of a plurality of discrete pulses.

Returning to FIG. 9a, drug delivery device 300 includes a first dose setting mechanism 302 situated within the drug delivery device outer housing 320 and operably connected to a primary reservoir 5 holding a first medicament 1. Similarly, drug delivery device 300 further comprises the second dose setting mechanism 304 also situated within the drug delivery device outer housing 320 and operably connected to a secondary reservoir 6 holding a second medicament 2. Preferably, the fixed dose piston rod 316 is positioned internal to the moving rack 314 of the second dose setting mechanism 304 and is operably connected to the secondary reservoir or cartridge 6 holding the second medicament 2. More preferably, and as illustrated in FIG. 9a, the fixed dose piston rod 316 comprises a distal end 318 and this distal end 318 abuts a first proximal surface of a stopper 20 of a cartridge or reservoir 6 containing the second medicament 2. Referring to both FIGS. 8 and 9a, the drug delivery device 300 also includes a single dose setter 306 that is operably coupled to the variable dose setting mechanism 302. A collar 308 is disposed on the variable dose setting mechanism 302 and a linkage component 310 is disposed on the fixed dose setting mechanism 304. The dose button 332 is situated at the proximal end of the variable dose setting mechanism 302.

Similar to the drug delivery device 200 illustrated in FIGS. 4a-k, the linkage component 310 of delivery device 300 comprises a pin sleeve 307 and a pin 309. The collar 308 of the variable dose setting mechanism 302 may be fixed to a dial sleeve and/or dose setter 306 of the dose setting mechanism 302. The pin sleeve 307 and pin 309 are fixed relative to the movable rack 314 such that the pin sleeve 307 remains rotationally constrained as the collar 308 rotates relative to the body 320 of the device 300. Similar to the examples described above, the pin sleeve 307 and pin 309 can impart lifting forces (for dose setting) or lowering forces (for dispense) to the second dose setting mechanism 304 via the pin 309 interaction with the collar 308.

Similar to collar 208, the collar 308 comprises a groove 322 that has a plurality of flat sections 340 a-d and a plurality of helical sections 350 a-d. (e.g., see FIGS. 8, 9h, 10a). In particular, groove 322 has four flat thread sections 340 a-d and four helical thread sections 350 a-d. As described above, during dose setting steps, the flat thread sections 340 a-d result in the pin 309 being pulled upwards (proximally) due to the dialing of dose setter 306. The helical thread sections 350a-d may be the same pitch as the dial sleeve of the variable dose setting mechanism 302 and so would result in the collar 308 rotating past the pin (and thus not loading the second medicament) as the dose setter 306 is rotated. In particular, with reference to FIGS. 9a-b, during a dose dialing step, when the pin 309 engages the flat helical sections 340 a-d on the collar 308, load is transferred to move the pin sleeve 307 (and hence the fixed dose setting mechanism 304) proximally in direction 334 at the same rate as the dose setter 306 translates proximally away from the outer housing 320. However, when the pin 309 is located in the helical sections 350 a-d of thread on the collar 308, no load is transferred and so no proximal movement of the fixed dose setting mechanism 304 occurs. Note that while the FIGS. 8-10 depicts a collar 308 comprising four flat sections 340 a-d and four helical sections 350 a-d, more or fewer flat and/or helical sections are possible. In addition, during a particular dose setting step, not all of the helical or flat thread sections may be used to administer a set dose.

The setting and dispensing phases of drug delivery device 300 are depicted in detail in FIGS. 9a-k. In particular, FIGS. 9a-h each depict various points during setting of the drug delivery device 300, and FIGS. 9f-k each depict various points during dispense. To begin, FIG. 9a illustrates a start position of the drug delivery device 300. In this start position, the device 300 is in a position with the variable dose setting mechanism 306 at a zero dose position and the fixed dose setting mechanism 304 also at a zero dose position. In this zero dose position, the pin 309 of the linkage component 310 remains resides within a first helical portion 350a of the groove 322.

Figure 9B:
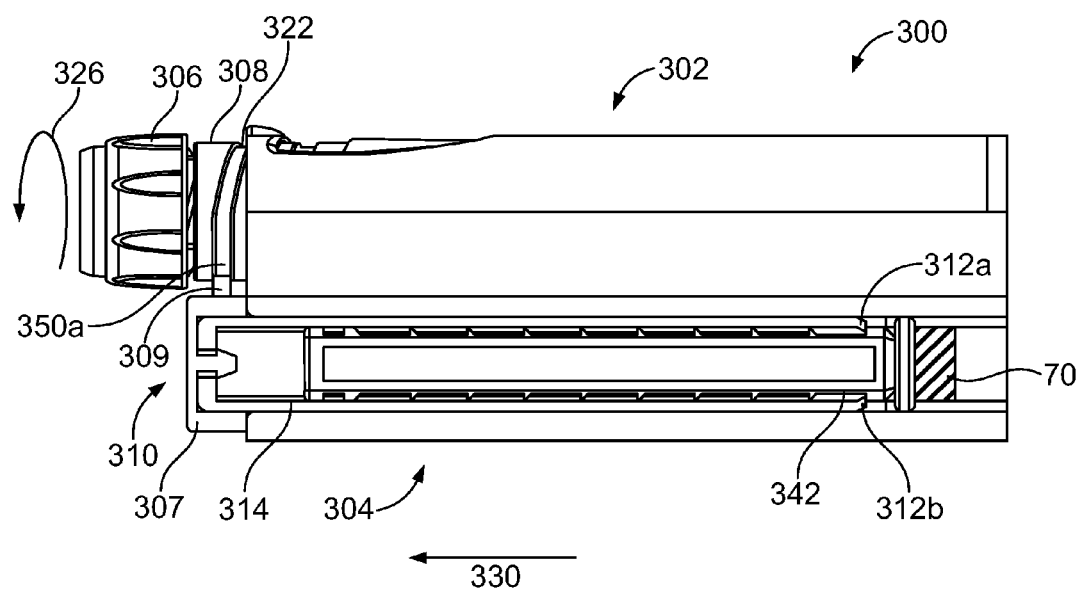

As shown in FIG. 9b, when a user begins to rotate the dose setter 306 in rotational direction 326, the pin 309 is in the collar groove 322 and, in particular, will subsequently move from the first helical section 350a of the groove 322 into the first flat thread section 340a. In this example, the first helical section 350a is the same pitch as the dial sleeve of the variable dose setting mechanism 302 and therefore results in the collar 308 rotating past the pin 309 and not loading the fixed dose setting mechanism 304. In other words, as the pin 309 moves through this first helical section 350a, the fixed dose setting mechanism 304, and hence the movable rack 314, does not move in the proximal direction 330. As such, the movable rack 314 and its corresponding one way ratchet features 312 a,b do not move along the outer surface 342 of the fixed dose piston rod 316.

Figure 9C:
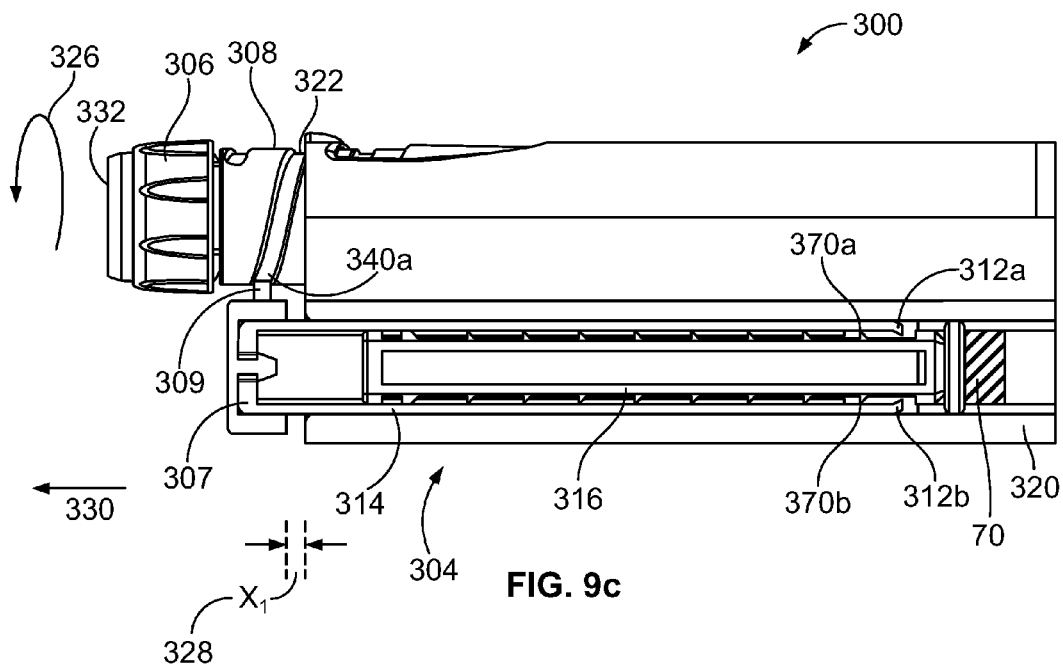

FIG. 9c illustrates a dose setting step where the pin 309 has just travelled through a first flat section 340a of the groove 322 and begins to enter the second helical thread section 350b. With reference to FIGS. 9b and 9c, as the pin 309 travels through the first flat section 340a of the groove 322, the fixed dose setting mechanism 304 moves axially in the proximal direction 330 by an amount X1 328. Rotation of dose setter 306 continues to set the variable dose of the first medicament 1 contained within the first reservoir 5 and but has not moved the moving rack 314 in prioximal direction 330 far enough to reach 'ratchet point 1' (i.e., the first element set 370 a,b), and hence does not set the fixed dose of the second medicament 2 contained within the second reservoir 6. Therefore, at this point in the dose setting procedure, if the user were to attempt to administer the set dose as illustrated in FIG. 9c, only a small amount of the first medicament 1 would be administered. None of the second medicament 2 would be administered since the one way ratchet arms 312 a,b of the moving rack 314 have not yet moved far enough in the proximal direction 330 for the arms 312 a,b to have over come the first ratchet element set provided near the distal end 318 of the fixed dose piston rod 318. As such, if the dose button 332 on the variable dosing mechanism 302 were pushed to administer this set dose, the moving rack 314 would merely move distally to its original start position (as illustrated in FIG. 9a-b) but would not engage the fixed dose piston rod 316 so as to move the piston rod in the distal direction.

Figure 9D:
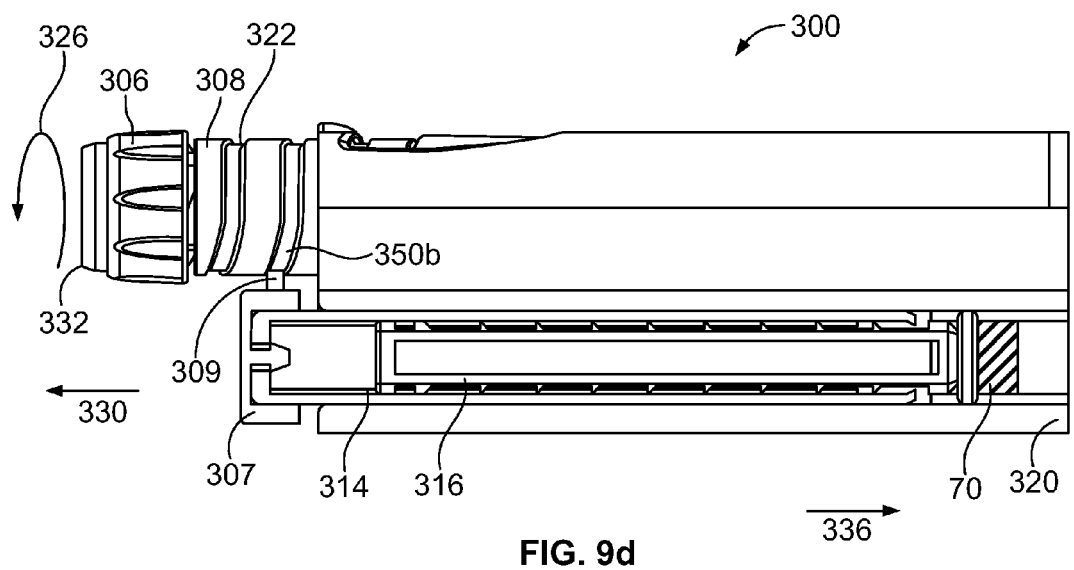

As shown in FIG. 9d, after a given amount of further rotation of the dose setter 306 in rotational direction 326, the pin 309 enters and runs in the second helical portion 350b of the groove 322 provided along the collar 308. During this additional dose setting step, no axial load is imparted on the pin 309 and therefore on the fixed dose setting mechanism 304. Therefore, the pin sleeve 307 and hence the movable rack 314 do not move in the proximal direction 330. Again, as such, if the dose button 332 on the variable dosing mechanism 302 were pushed to administer this set dose, the moving rack 314 would merely move distally to its original start position (as illustrated in FIG. 9a-b) but would not engage the fixed dose piston rod 316 so as to move the piston rod 316 in the distal direction 336.

Figure 9E:
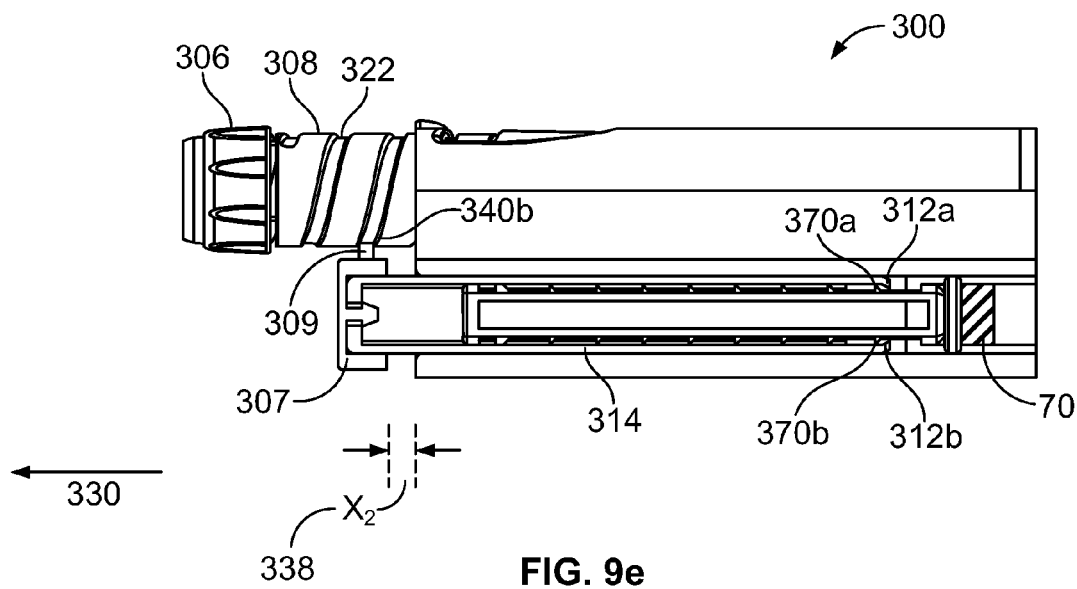

Further rotation of the dose setter 306 then forces the pin 309 to travel from the second helical section 350b through to the second flat section 340b of the groove 322. This additional dose setting step is illustrated in FIG. 9e. Referring now to FIG. 9e, as the pin 309 travels through this second flat section 340b and begins to enter the third helical section 350c, the movable rack 314 of the fixed dose setting mechanism 304 moves axially for a second time in the proximal direction 330. As such, the total distance that the movable rack 314 has now moved in the proximal direction is X2 338. However, as illustrated in FIG. 9e, the one way ratchet features 312 a,b still have not moved sufficiently in the proximal direction 330 so as to overcome the first ratchet element set 370 a,b. As such, the first predetermined fixed dose as defined by the position of the first ratchet element set of the second medicament 2 still has yet to be set. Therefore, if a user were to now administer this set dose illustrated in FIG. 9e, only the set dose of the first medicament 1 and none the second medicament 2 from the second reservoir 6 would be administered. If administered in this position, the movable rack 314 would merely move in the distal direction 336 the distance X2 338 with no consequent interaction with the fixed dose piston rod 316 and therefore no dispense of the second medicament 2.

Figure 9F:
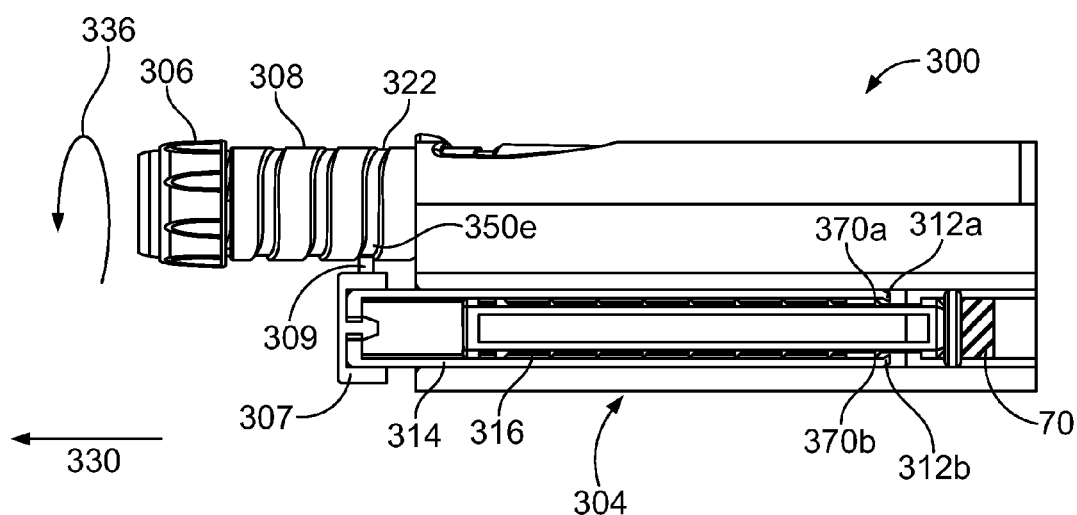

As shown in FIG. 9f, after yet additional rotation of the dose setter 306 in rotational direction 326, the pin 309 enters and runs in the third helical portion 350c of the groove 322 on the collar 308. During this dose setting step, again, no axial load is imparted on the fixed dose setting mechanism 304. Therefore, the pin sleeve 307 and hence the movable rack 314 does not move in the proximal direction 330.

Figure 9G:
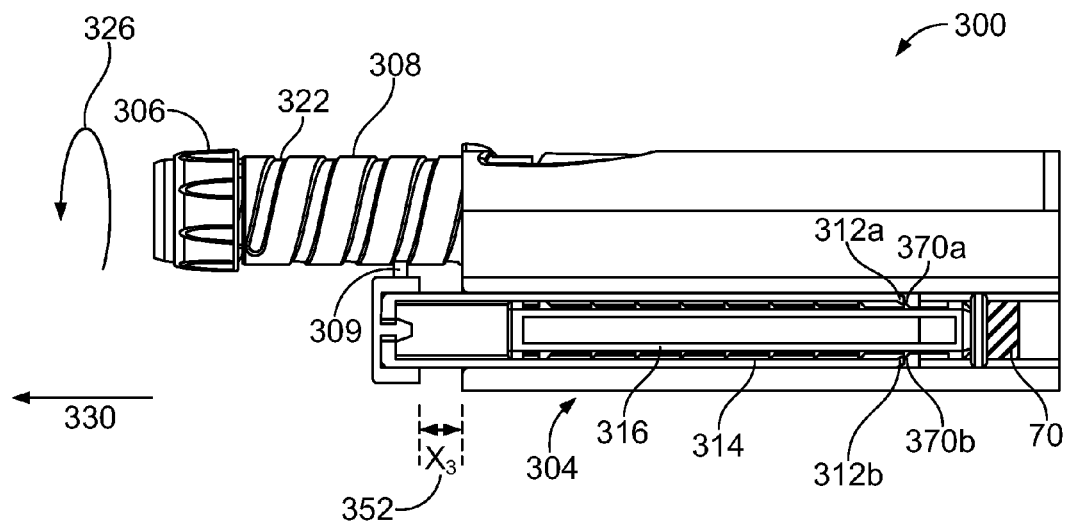

As illustrated in FIG. 9g, further rotation of the dose setter 306 in rotational direction 326 forces the pin 309 to travel through the third flat section 340c of the groove 322 and begin to enter into the fourth helical section 350d. As the pin 309 travels through this third flat section 340c, the fixed dose setting mechanism 304 moves axially for a third time in the proximal direction 330 and the total distance moved by the rack 314 is designated by X3 352. As illustrated, the one way ratchet arms 312 a,b have moved again in the proximal direction 330 and have now moved past the first ratchet element set 370 a,b provided on the fixed dose piston rod 316. Therefore, the drug delivery device 300 illustrated in FIG. 9g has now been set to administer a combination dose of both the first medicament 1 contained in the first reservoir 5 and a first predefined dose of the second medicament 2 contained within the second reservoir 6. Therefore, in the fixed dose setting mechanism 304 illustrated in FIG. 9g, the distance X3 352 defines the total proximal movement required by the moving rack 314 in order to set the first fixed dose of the dose setting mechanism 304. As such, if a user were to now administer this set dose, the set dose would now comprise a combination dose of the first medicament 1 and the first fixed dose of the second medicament 2.

Figure 9H:
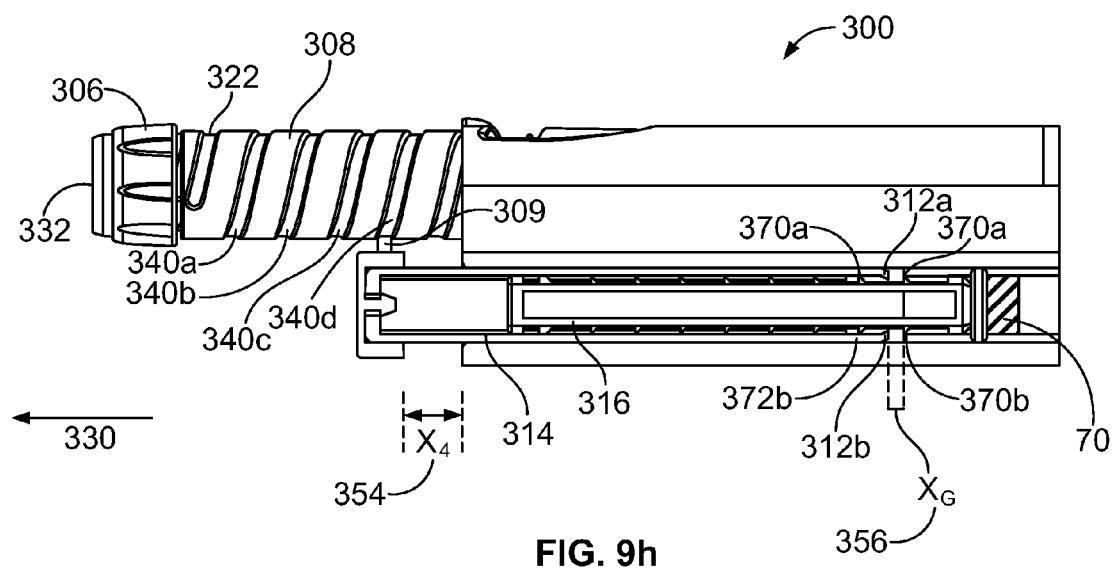

After the first predetermined fixed dose of the second medicament 2 has been set, the dose setter 306 may be rotated further to set a higher dose of the first medicament 1. For example, further rotation of the dose setter 306 then forces the pin 309 to travel through yet another helical section 350d and then a subsequent fourth flat section 340d. With reference to FIG. 9h, as the pin 309 travels through this fourth flat section 340d, the fixed dose setting mechanism 304 moves axially for yet another time in the proximal direction 330 and now resides a total distance X4 354 following this final dose setting procedure. As illustrated, the one way ratchet arms 312 a,b have moved an additional distance defined by a gap (i.e., XG 356) past the first ratchet element set 370 a,b but have not moved past the second ratchet element set 372 a,b. Therefore, the fixed dose setting mechanism 304 is still set to administer the first fixed dose of the second medicament 2 but has not moved a sufficient amount to set the second fixed dose as defined by the position of the second ratchet element set 372 a,b. As such, if a user were to now administer this set dose, the set dose of the first medicament 1 and the first fixed dose of the second medicament 2 as defined by the first ratchet element set 370 a,b would be administered.

After setting the desired dose of the first medicament 1, the user may dispense the medicament. As will be explained with reference to FIGS. 10a-h and FIG. 11, dose administration of this set combination dose occurs by way of a continuous administration of the first medicament 1 along with a plurality of discrete pulses of the second medicament 2. For example, FIG. 11 illustrates a dose profile 500 comprising a pulsed delivery of the dose that has been set by the drug deliver device 300 illustrated in FIG. 9h.

To begin to administer this set dose, referring to FIG. 9h, the user pushes on the dose setting button 332. This action causes the dose setter 306 (and therefore the collar 308) to rotate in rotational direction 334 and therefore translate in a distal direction towards the outer housing 320 and this movement in distal direction 336 may begin dispense of the first medicament 1. As illustrated, with the pin initially residing in the fourth flat section 340*d*, the fixed dose setting mechanism will move in the proximal direction so as to close the gap XG so that the ratchet arms will abut a proximal side of the first ratchet elements 370*a, b*. Since the movement of the moveable rod 314 imparts no movement of the piston rod 316, during this initial proximal movement, no second medicament will be administered and only the first medicament will be administered. This initial distal movement of the fixed piston rod in the distal direction accompanied with the commencement of administration of the first medicament 1 is illustrated by the start of the dose 502 of the profile illustrated in FIG. 11.

Further movement in the rotational direction 334 and thus distal direction 336 causes the collar 308 to push against the pin 309 and moves the pin 309 through the fourth flat section 340*d* and into the fourth helical section 350*d*. This action continues to dispense the first medicament 1 but not of the second medicament 2. As such, the piston rod 316 does not move in the distal direction and no administration of the second medicament 2 occurs during this step where the pin 309 resides in the fourth helical section 350*d*. This first dosing step of administering only the primary medicament as the pin moves from the fourth thread section 350*d* and through the fourth helical section 340*d* is illustrated as the complete dosing step 502 in the profile 500 illustrated in FIG. 11.

Figure 10A:
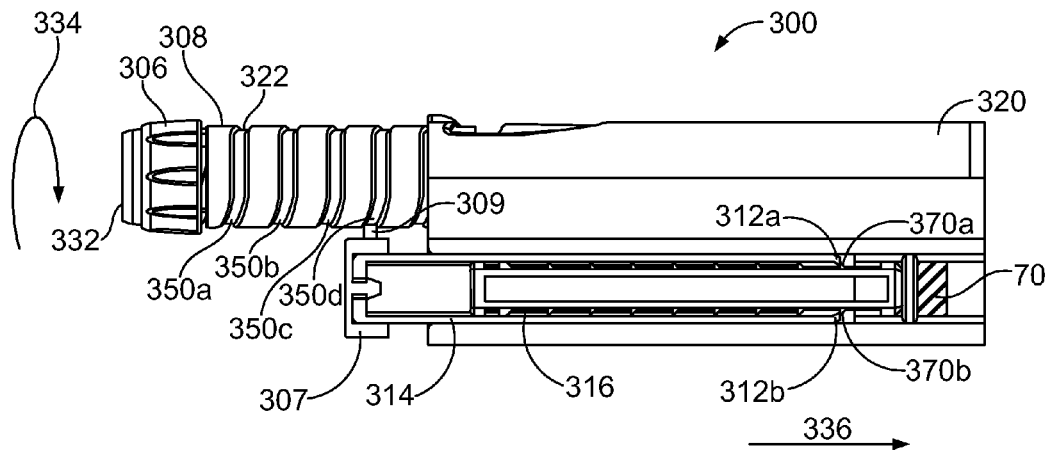
FIGS. 10a-h illustrates the drug delivery device illustrated in FIG. 8 at various phases of dose administration.
Figure 10B:
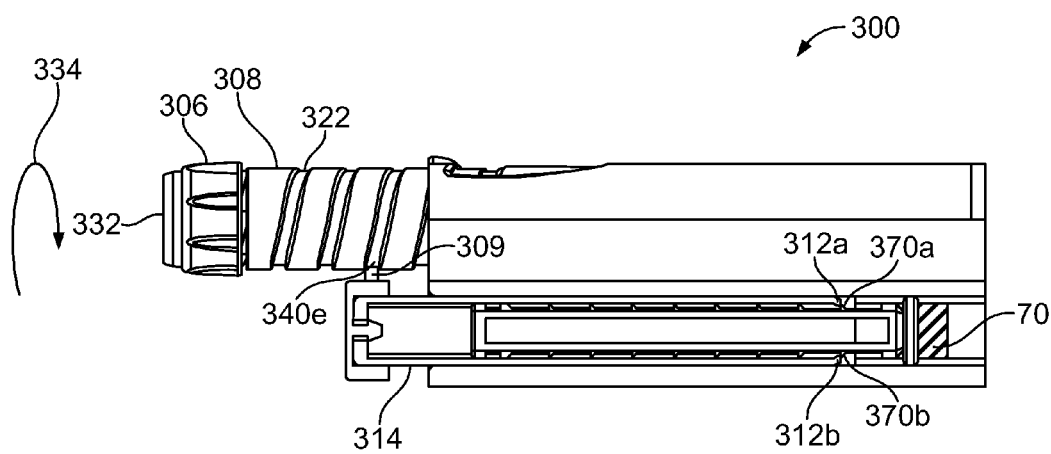
Figure 10C:
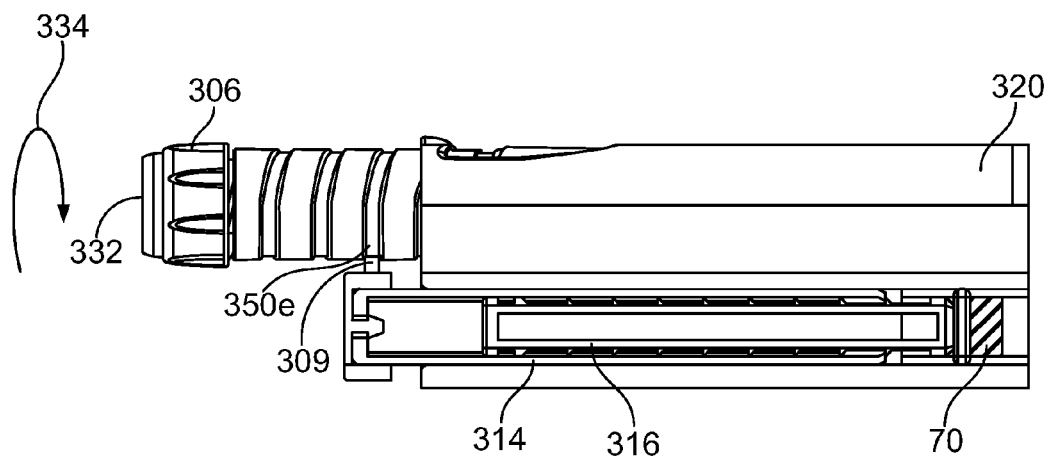

Continued pressure on the dose button 332 causes further rotation of the collar 308 during dose dispense. This forces the pin 309 to move out of the fourth helical section 340*d* and into the third flat thread section 350*d* to initiate the first pulsed dose of the first medicament. For example, FIG. 10*b* illustrates where the pin 309 is just about to exit the fourth helical section 350*d* and enter the third flat thread section 340*c*. With continued pressure on dose button 332, the pin 309 enters the third flat section 340*c*. Since the one way ratchet arms 312 *a,b* of the moving rack 314 is now engaged with the first ratchet element set 370 *a,b* on the piston rod 316, continued distal movement of the piston rod acts on the stopper 20 of the cartridge to thereby initiate a pulsed dispense of the second medicament 2 from the cartridge 6. This situation is illustrated in FIG. 10*c*. However, the entire predetermined fixed dose will not be administered since the pin 309 will reside in the third flat section 340*c* for only a discrete period of time. Consequently, the resulting dispense will comprise only a discrete pulse of the second medicament 2 where the pulse is initiated only during the period of time where the pin 309 first enters in the third flat section 340*c* and the pulse is completed when the pin 309 exists the third flat section 340*c* and begins to enter the third helical section 350*c* of the groove 322. As such, during this pulsing cycle, the administered medicament will comprise a combination dose of a continued administered first medicament 1 and a pulsed administration of a proportion of the dose of the second medicament 2. The end of this first pulse is illustrated in FIG. 10*c* where pin 309 has now moved through the third flat section 340*c* and into the third helical section 350*c*. During this step, the moving rack 314 has moved distally a distance that is equal to the distance of X3 352 minus X2 338. Administration of this first pulse of the second medicament is illustrated by the pulse 504 of profile 500 illustrated in FIG. 11.

Figure 10D:
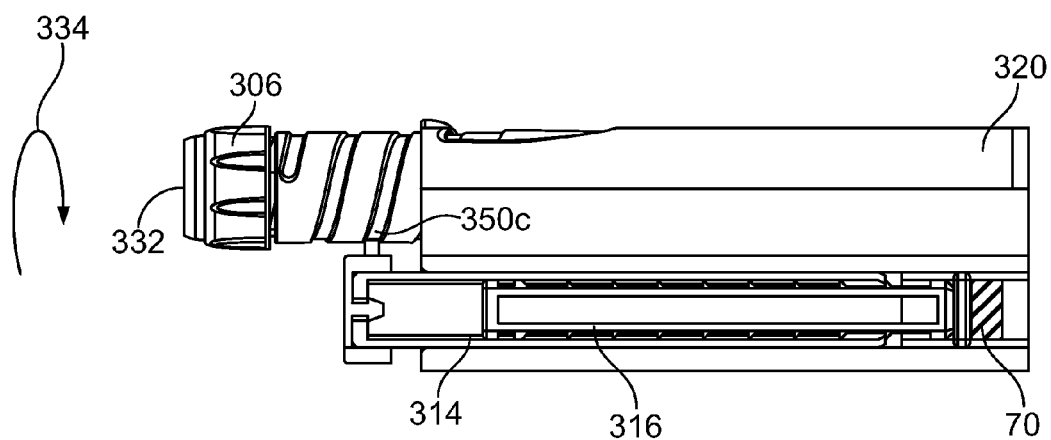
Figure 10E:
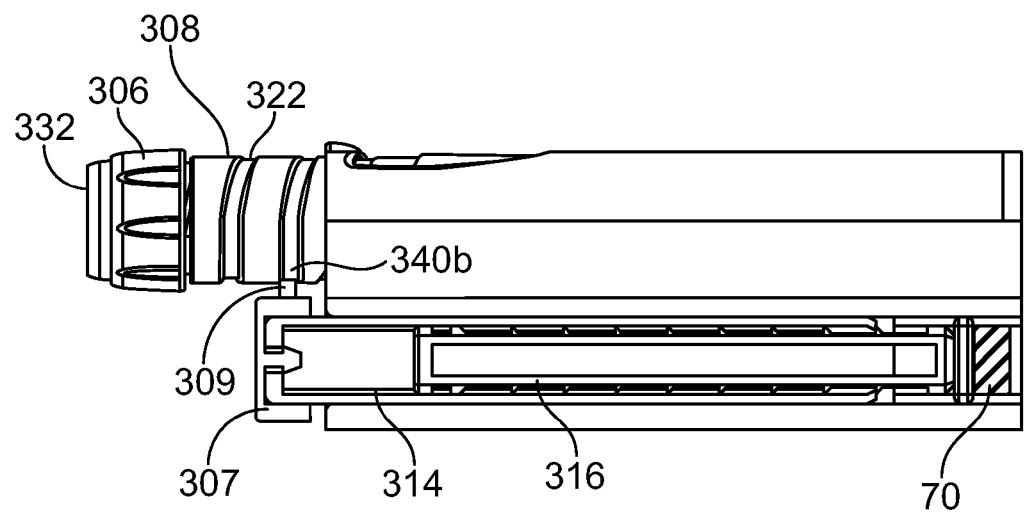

FIG. 10*d* illustrates the next step in the dispense stroke and this is illustrated as dosing step 506 in FIG. 11. During this step 506, as the dose setter 306 continues to rotate and cause the dose dial sleeve to translate back into outer housing 320, the pin 309 next enters the third helical portion 350*c* of the groove 322. As such, no force is imparted onto the movable rack 314 and therefore the only medicament administered during this step is the first medicament 1 by way of the variable dose setting mechanism 302. Thereafter, once the pin 309 exists this third helical section 350*c*, it then enters the second flat section 340*b* of the groove 322 and another pulse of the second medicament 2 will begin to be initiated. Administration of this second pulse of the second medicament 2 is illustrated in the FIG. 10*e* where the system 300 is illustrated with the pin 309 already having traversed the second flat thread section 340*b* and illustrates the pin 309 now entering the second helical thread section 350*b*. Administration of this second pulse is illustrated by dose 508 in FIG. 11.

Figure 10F:
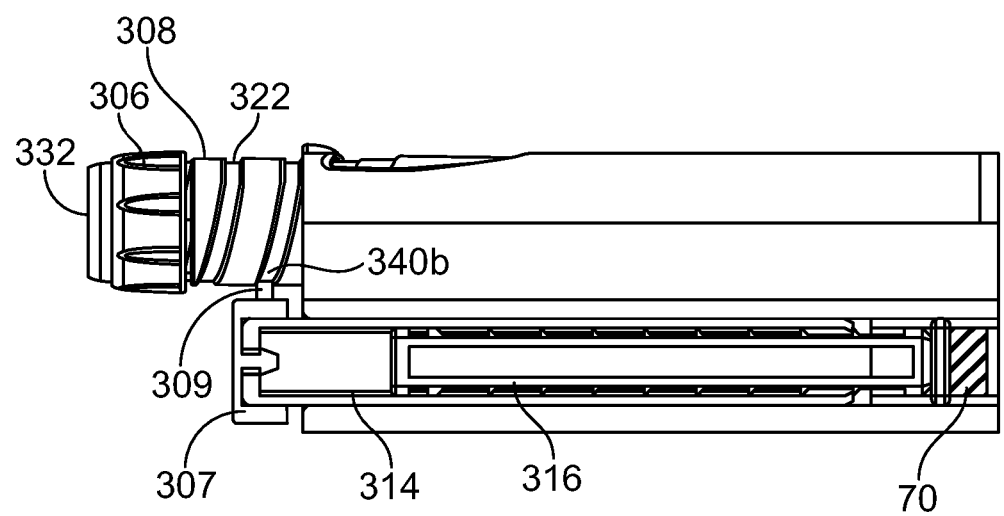

Further rotation of the dose setter 306 during dispense causes the pin 309 to exit the second flat section 340*b* and enter the second helical section 350*b* of the groove 322. This is illustrated in FIG. 10*f* and is represented by the dose 510 in the profile 500 in FIG. 11. During this dose administration step, as the dose setter 306 continues to rotate and cause the dose dial sleeve to translate back into outer housing 320, the pin 309 exits the second helical thread section 350*b* and then begins to enter the first flat portion 350*a* of the groove 322. As such, no force is imparted onto the movable rack 314 and therefore the only medicament administered during this step 510 is the first medicament 1 by way of the variable dose setting mechanism 302.

Figure 10G:
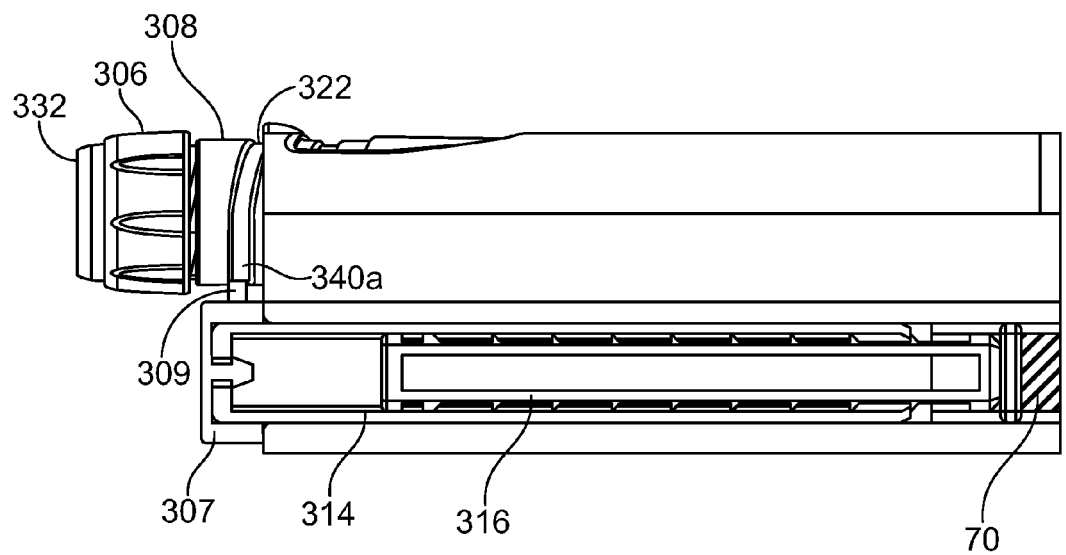

FIG. 10*g* illustrates the pin 309 after it has traversed the final or first flat thread section 340*a* and is just about to re-enter the final helical section 350*a*. This third and final dose pulse of the second medicament 2 is illustrated as dose 512 in FIG. 11. As illustrated, FIG. 10*g* shows the pin 309 after the drug delivery device 300 has administered the third pulse 512 and the pin residing in the first helical section 350*a* of groove 322. Further pressing the dose button will move the pin through the first helical section 350*a* to administer the last remaining dose of the first medicament and this is represented by dose 514 illustrated in FIG. 11.

Figure 10H:
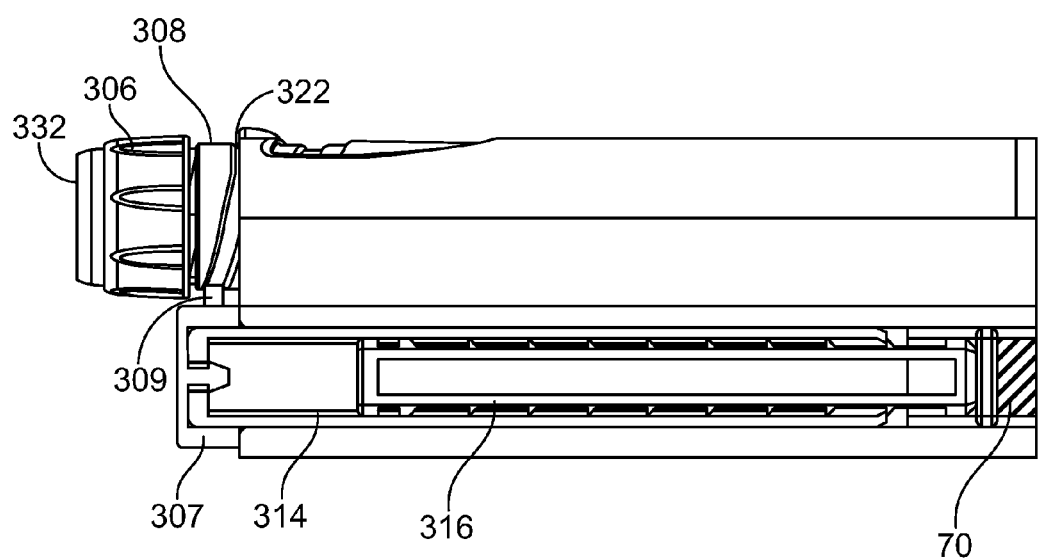

When the dose setter 306 is fully depressed back to its starting position (i.e., pre-set position as illustrated in FIG. 9*a*), as shown in FIG. 10*h*, both the first medicament 1 and the second medicament 2 have been fully dispensed where the first medicament 1 is dispensed in a continuous manner while the second medicament has been dispensed in a pulsed manner. In this illustrated, the second medicament has been dispensed via three discrete pulses: pulses 504, 508, and 512 illustrated in FIG. 11. FIG. 10*h* illustrates the drug delivery device 300 in a final dose dispense position.

Beneficially, the various flat sections 340*a-d* and helical sections 350 *a-d* of the groove 322 can be modified in order to achieve a desired dose profile. For example, the groove 322 may have more flat sections and more helical sections, and thus may result in more steps in the pulsed, fixed dose profile. Additionally, the angular arc of the flat sections can be varied to change the relative duration of the individual pulses, as required.

One advantage of a drug delivery device having a collar such as collar 308 relates to the fact that the delayed setting of the second medicament means that a user may perform a priming step with only the first medicament (and not the second medicament). This priming can be carried out as many times as necessary (each with a volume up to the minimum threshold of the first medicament) without dispensing any of the second medicament. For a multi-dose drug delivery device, a profile of this type may, for example, be beneficial where (i) the second medicament dose not require repeated priming, (ii) the simultaneous priming of the first and second medicament might mask an unsuccessful priming of the first medicament, or (iii) the second medicament is a particularly expensive compound that preferably is not wasted. Other examples are possible as well.

As described above, prior to each dose, the user could potentially vary the threshold at which the full dose of the second medicament is set, or the user may leave the threshold unchanged from its previously set value. Similarly, the half dose threshold could also potentially be varied by a user or by a prescribing healthcare professional prior to handover of the device.

As mentioned above, in some examples of the drug delivery devices described above, the device could be configured to have the fixed dose increase in a plurality of steps, such as two or more steps, each of which is set when an associated defined threshold of the first medicament is set.

The disclosed drug delivery devices may be suited towards a modular disposable or re-usable platform in terms of managing drug wastage. This is because there is a risk of one medicament being finished before the other unless there is a strict 1:1 ratio between the two medicaments. However, where each side is resettable, new medicament reservoirs can be inserted and the device can continue to be used. Possible embodiments for a modular disposable platform could involve, but are not limited to, the replacement of the entire device mechanism fitted with a new primary pack. Suitable re-engagement features may be integrated into the device platform to facilitate the alignment and fastening of the individual device mechanisms together in a robust and user friendly fashion. It is possible that such features could be arranged to define the permissible functionality of the two individual elements on their own.

A possible re-usable platform would feature spindles that could be back wound into their respective devices once they had reached the limits of travel, such as those known in the art. In addition to this functionality, the platform would feature a means of replacing the medicament reservoir or reservoirs after the resetting of one or both spindles.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A drug delivery device comprising:
   a variable dose setting mechanism wherein the variable dose setting mechanism is operably coupled to a primary reservoir holding a first medicament;
   a fixed dose setting mechanism comprising a fixed dose piston rod, wherein the fixed dose piston rod is operably coupled to a secondary reservoir holding a second medicament, wherein the secondary reservoir is positioned side-by-side to the primary reservoir;
   a rotatable single dose setter operably coupled to the variable dose setting mechanism such that of the user rotates the single dose setter during a dose setting step a variable dose of the first medicament is set and automatically a fixed dose of the second medicament is set by means of;
   a ring-shaped collar disposed on the variable dose setting mechanism and;
   a linkage component disposed on the fixed dose setting mechanism, wherein the linkage component is capable of engagement with the collar, wherein the collar comprises a groove, and wherein the linkage component comprises a pin that is slidably engageable with the groove.

2. The drug delivery device of claim 1, wherein during a dose setting step, the drug delivery device automatically sets a fixed dose of the second medicament upon setting of a target dose of the first medicament using the single dose setter.

3. The drug delivery device of claim 1, wherein the fixed dose setting mechanism comprises an axially-set dose setting mechanism.

4. The drug delivery device of claim 1, wherein the groove of the collar comprises at least two sections, and wherein the pin of the linkage component is slidably engageable with at least one section of the groove.

5. The drug delivery device of claim 4, wherein the groove comprises at least one helical section and at least one flat section, and wherein the pin is configured to slidably engage with the groove.

6. The drug delivery device of claim 1, wherein the fixed dose setting mechanism comprises an axially movable rack, the movable rack is operably coupled to both the pin and to the fixed dose piston rod,
   wherein, during a dose setting step, rotation of the collar forces the pin to move through at least one section of the groove and thereby cause the axially moveable rack to move in a proximal direction.

7. The drug delivery device of claim 5, wherein, during a dose setting step, rotation of the collar forces the pin to move through at least one section of the groove and thereby move the axially moveable rack in a proximal direction and to thereby set a first predetermined fixed dose.

8. The drug delivery device of claim 7, wherein the first predetermined fixed dose is set when a one way ratchet arm of the axially moveable rack moves in a proximal direction so as to slide over a ratchet element set, the ratchet element set positioned along an outer surface of the fixed dose piston rod.

9. The drug delivery device of claim 8, wherein, during a dose setting step, rotation of the collar forces the pin to move through the groove and thereby moves the moveable rack axially in a proximal direction and to thereby set a second predetermined fixed dose, the second predetermined fixed dose larger than the first predetermined fixed dose.

10. The drug delivery device of claim 1, wherein the drug delivery device is capable of delivering medicament according to a dose profile, wherein the dose profile comprises a fixed dose of the second medicament that is delivered by way of at least one discrete pulse of the second medicament but only after a minimum dose of the first medicament is set.

11. The drug delivery device of claim 10, wherein the drug delivery device is capable of delivering medicament according to a dose profile wherein the dose profile comprises a combination dose of a variable dose and the pulsed delivery of the fixed dose of the second medicament after a minimum dose of the first medicament is set.

12. The drug delivery device of claim 1, wherein the groove has a plurality of sections, wherein a first section comprises at least one generally flat section and wherein a second section comprises at least one helical section, and wherein the pin is slidably engageable with the groove.

13. The drug delivery device of claim 1, wherein the groove has a plurality of sections, wherein a first section is a first helical section having a first pitch, and wherein a second section is a second helical section having a second pitch different from the first pitch.

14. The drug delivery device of claim 1, wherein the groove has a plurality of sections, wherein a first section is a generally flat section and wherein a second section is a helical section, and wherein the linkage component comprises a pin sleeve, and wherein the pin is slidably engageable with the groove.

* * * * *